United States Patent
Chateau et al.

(10) Patent No.: US 7,745,195 B2
(45) Date of Patent: *Jun. 29, 2010

(54) METHOD FOR THE PREPARATION OF AN EVOLVED MICROORGANISM FOR THE CREATION OR THE MODIFICATION OF METABOLIC PATHWAYS

(75) Inventors: Michel Chateau, Riom (FR); Benjamin Gonzalez, Riom (FR); Isabelle Meynial-Salles, Fourquevaux (FR); Philippe Noel Paul Soucaille, Deyme (FR); Olivier Zink, Mulhouse (FR)

(73) Assignee: Metabolic Explorer, Saint Beauzire (FR)

( * ) Notice: Subject to any disclaimer, the term of this patent is extended or adjusted under 35 U.S.C. 154(b) by 519 days.

This patent is subject to a terminal disclaimer.

(21) Appl. No.: 10/781,499

(22) Filed: Feb. 18, 2004

(65) Prior Publication Data
US 2005/0054060 A1  Mar. 10, 2005

(30) Foreign Application Priority Data

| Feb. 18, 2003 | (FR) | ................................. 03 01924 |
| May 14, 2003 | (FR) | ................................. 03 05768 |
| May 14, 2003 | (FR) | ................................. 03 05769 |
| Nov. 6, 2003 | (FR) | ................................. 03 13054 |

(51) Int. Cl.
*C12N 1/00* (2006.01)
*C12N 1/36* (2006.01)
(52) U.S. Cl. .................... 435/243; 435/245
(58) Field of Classification Search ................. 435/245
See application file for complete search history.

(56) References Cited

U.S. PATENT DOCUMENTS

| 3,071,518 | A | 1/1963 | Scherr et al. |
| 4,071,405 | A | 1/1978 | Soda et al. |
| 5,344,767 | A | 9/1994 | Boullais et al. |
| 6,368,793 | B1 | 4/2002 | Hoch et al. |
| 2002/0177196 | A1 | 11/2002 | Maier |
| 2005/0124010 | A1* | 6/2005 | Short et al. ................. 435/7.23 |

FOREIGN PATENT DOCUMENTS

| EP | 0699748 | 3/1996 |
| GB | 2174390 | 11/1986 |
| JP | 2222692 | 9/1990 |
| JP | 2000157267 | 6/2000 |
| WO | WO 93/17112 | * 9/1993 |
| WO | 00/34433 | 6/2000 |
| WO | WO 02/18613 | 3/2002 |
| WO | WO 02/46451 | 6/2002 |
| WO | WO 02/051231 | 7/2002 |
| WO | 03/004656 | 1/2003 |

OTHER PUBLICATIONS

Nakamori et al. (Applied Microbial Biotechnology, vol. 52, pp. 179-185, 1999).*
Richaud et al. (J. Biological Chemistry. Dec. 25, 1993; 268(36):26827-26835).*
Database WPI Abstract No. 2000-485 354, XP-002265367, Week 200043, Derwent Publications Ltd.
Database EMBL, Accession No. AF220150, XP-002185277, Jan. 17, 2001.
Database EMBL, Accession No. KO1546, XP-002274156, Jun. 13, 1985.
Database EMBL, Accession No. )97CC7, XP-002274157, Oct. 1, 2001.
Arnold et al. (1997) "Optimizing Industrial Enzymes by Directed Evolution" in Advances in Biochemical Engineering 58:1-14, Springer, Berlin.
Flavin et al. (1967) Biochim Biophys. Acta 132:400-405.
May et al. (2000) Nature Biotechnology 18:317-320.
Smith et al. (1969) Biochim. Biophys. Acta 184:130-138.
Weissbach et al. (1991) Molecular Microbiology 5:1593-1597.
International Patent Application Publication No. W002/083892, Oct. 24, 2002.
European Patent Application 0 519 113 Al, Dec. 23, 1992.
United Kingdom Patent Application GB 2 075 055 A, Nov. 11, 1981.
Duchange et al. (1985) EMBL, XP002274156.
Kase et al. (1975) Agr. Biol. Chem. 39:153-160.
Kawashima et al. (2001) EMBL, XP002274157.
Nakamori et al. (1991) Appl. Microbiol. Biotechnol. 52:179-185.
Anderson, E.H. (1946), Growth requirements of virus-resistant mutants of *Escherichia coli* strain "B" Proc. Natl. Acad. Sci. USA 32:120-128.
A Baudin, O Ozier-Kalogeropoulos, A Denouel, F Lacroute, and C Cullin (1993), A simple and efficient method for direct gene deletion in *Saccharomyces cerevisiae*, Nucl. Acids Res., 21: 3329-3330, 1993.
Brachmann CB, Davies A, Cost GJ, Caputo E, Li J, Hieter P, Boeke JD. (1998), Designer deletion strains derived from *Saccharomyces cerevisiae* S288C: a useful set of strains and plasmids for PCR-mediated gene disruption and other applications. Yeast. 14:115-32.
Datsenko, K.A.; Wanner, B.L. (2000), One-step inactivation of chromosomal genes in *Escherichia coli* K-12 using PCR products. Proc. Natl. Acad. Sci. USA 97: 6640-6645.
Schaefer, U., Boos, W., Takors, R., Weuster-Botz, D. (1999), Automated sampling device for monitoring intracellular metabolite dynamics, Anal. Biochem. 270: 88-96.
Marcia K. Allen and Charles Yanofsky, "A Biochemical and Genetic Study of Reversion with the Ag-Gene A-Protein System of *Escherichia coli* Tryptophan Synthetase," Department of Biological Sciences, Genetics 48:1065-183, Aug. 1963,University, Stanford University.

* cited by examiner

*Primary Examiner*—Robert B. Mondesi
*Assistant Examiner*—Khatol Sahanan-Shah
(74) *Attorney, Agent, or Firm*—Baker Donelson Bearman, Caldwell & Berkowitz

(57) ABSTRACT

The present invention is directed to a method for the preparation of evolved microorganisms permitting the creation or modification of metabolic pathways. Strains of evolved microorganisms and evolved genes obtained by the method are also provided. The invention is also directed to the use of evolved microorganisms, genes or proteins in a biotransformation process.

19 Claims, 8 Drawing Sheets

Figure 1:
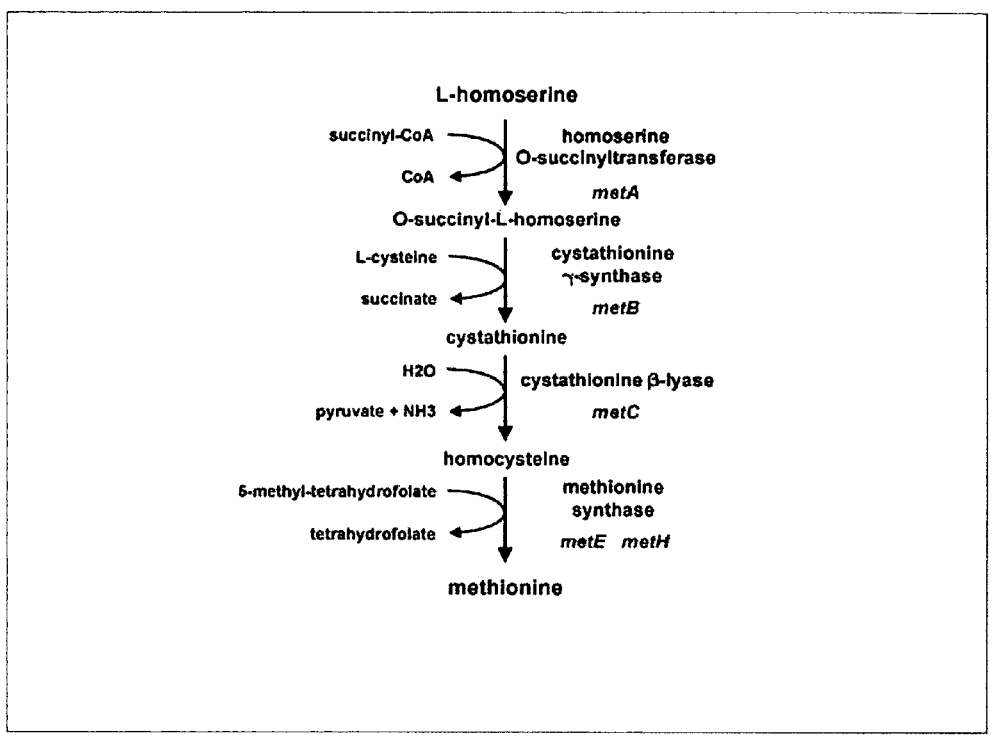

SEQUENCE LISTING

<160> NUMBER OF SEQ ID NOS: 42

<210> SEQ ID NO 1
<211> LENGTH: 100
<212> TYPE: DNA
<213> ORGANISM: Artificial Sequence
<220> FEATURE:
<223> OTHER INFORMATION: DmetER

<400> SEQUENCE: 1

```
tacccccgac gcaagttctg cgccgcctgc accatgttcg ccagtgccgc gcgggtttct      60
ggccagccgc gcgttttcag catatgaata tcctccttag                          100
```

<210> SEQ ID NO 2
<211> LENGTH: 100
<212> TYPE: DNA
<213> ORGANISM: Artificial Sequence
<220> FEATURE:
<223> OTHER INFORMATION: DmetEF

<400> SEQUENCE: 2

```
tgacaatatt gaatcacacc ctcggtttcc ctcgcgttgg cctgcgtcgc gagctgaaaa      60
aagcgcaaga aagttattgg tgtaggctgg agctgcttcg                          100
```

<210> SEQ ID NO 3
<211> LENGTH: 30
<212> TYPE: DNA
<213> ORGANISM: Artificial Sequence

```
<220> FEATURE:
<223> OTHER INFORMATION: MetER

<400> SEQUENCE: 3
ggtttaagca gtatggtggg aagaagtcgc                                           30

<210> SEQ ID NO 4
<211> LENGTH: 30
<212> TYPE: DNA
<213> ORGANISM: Artificial Sequence
<220> FEATURE:
<223> OTHER INFORMATION: MetEF

<400> SEQUENCE: 4
cccggggatg aataaacttg ccgccttccc                                           30

<210> SEQ ID NO 5
<211> LENGTH: 1161
<212> TYPE: DNA
<213> ORGANISM: Escherichia coli

<400> SEQUENCE: 5
atgacgcgta acaggccac catcgcagtg cgtagcgggt taaatgacga cgaacagtat           60
ggttgcgttg tcccaccgat ccatctttcc agcacctata actttaccgg atttaatgaa        120
ccgcgcgcgc atgattactc gcgtcgcggc aacccaacgc gcgatgtggt tcagcgtgcg        180
ctggcagaac tggaaggtgg tgctggtgca gtacttacta ataccggcat gtccgcgatt        240
cacctggtaa cgaccgtctt tttgaaacct ggcgatctgc tggttgcgcc gcacgactgc        300
tacggcggta gctatcgcct gttcgacagt ctggcgaaac gcggttgcta tcgcgtgttg        360
tttgttgatc aaggcgatga acaggcatta cgggcagcgc tggcagaaaa acccaaactg        420
gtactggtag aaagcccaag taatccattg ttacgcgtcg tggatattgc gaaaatctgc        480
catctggcaa gggaagtcgg ggcggtgagc gtggtgata cacccttctt aagcccggca         540
ttacaaaatc cgctggcatt aggtgccgat ctggtgttgc attcatgcac gaaatatctg        600
aacggtcact cagacgtagt ggccggcgtg gtgattgcta agacccggga cgttgtcact        660
gaactggcct ggtgggcaaa caatattggc gtgacgggcg gcgcgtttga cagctatctg        720
ctgctacgtg ggttgcgaac gctggtgccg cgtatggagc tggcgcagcg caacgcgcag        780
gcgattgtga ataccctgca aacccagccg ttggtgaaaa aactgtatca cccgtcgttg        840
ccggaaaatc aggggcatga aattgccgcg cgccagcaaa aaggctttgg cgcaatgttg        900
agttttgaac tggatggcga tgagcagacg ctgcgtcgtt tcctgggcgg gctgtcgttg        960
tttacgctgg cggaatcatt aggggagtg gaaagtttaa tctctcacgc cgcaaccatg        1020
acacatgcag gcatggcacc agaagcgcgt gctgccgccg ggatctccga cgcgctgctg      1080
cgtatctcca ccggtattga agatggcgaa gatttaattg ccgacctgga aaatggcttc      1140
cgggctgcaa acaaggggta a                                                1161

<210> SEQ ID NO 6
<211> LENGTH: 10
<212> TYPE: PRT
<213> ORGANISM: Escherichia coli

<400> SEQUENCE: 6

Met Glu Thr Thr His Arg Ala Arg Gly Leu
1               5                   10
```

<210> SEQ ID NO 7
<211> LENGTH: 1161
<212> TYPE: DNA
<213> ORGANISM: Escherichia coli

<400> SEQUENCE: 7

```
atgacgcgta acaggccac  catcgcagtg cgtagcgggt aaatgacga  cgaacagtat      60
ggttgcgttg tcccaccgat  ccatctttcc agcacctata  actttaccgg  atttaatgaa    120
ccgcgcgcgc atgattactc  cgtcgcggc  aacccaacgc  gcgatgtggt  tcagcgtgcg    180
ctggcagaac tggaaggtgg  tgctggtgca gtacttacta ataccggcat  gtccgcgatt    240
cacctggtaa cgaccgtctt  tttgaaacct ggcgatctgc  tggttgcgcc  gcacgactgc    300
tacgccggta gctatcgcct  gttcgacagt ctggcgaaac  gcggttgcta  tcgcgtgttg    360
tttgttgatc aaggcgatga acaggcatta cgggcagcgc  tggcagaaaa  acccaaactg    420
gtactggtag aaagcccaag  taatccattg ttacgcgtcg tggatattgc  gaaaatctgc    480
catctggcaa gggaagtcgg  ggcggtgagc gtggtggata  cacccttctt  aagcccggca    540
ttacaaaatc cgctggcatt  aggtgccgat ctggtgttgc attcatgcac  gaaatatctg    600
aacggtcact cagacgtagt  ggccggcgtg gtgattgcta aagacccgga  cgttgtcact    660
gaactggcct ggtgggcaaa  caatattggc gtgacgggcg  cgcgtttga  cagctatctg    720
ctgctacgtg ggttgcgaac  gctggtgccg cgtatggagc  tggcgcagcg  caacgcgcag    780
gcgattgtga ataccgtgca  aacccagccg ttggtgaaaa  aactgtatca  cccgtcgttg    840
ccggaaaatc agggggcatga aattgccgcg  cgccagcaaa  aaggctttgg  cgcaatgttg    900
agttttgaac tggatggcga  tgagcagacg ctgcgtcgtt  tcctgggcgg  gctgtcgttg    960
tttacgctgg cggcatcatt  aggggagtg  gaaagtttaa  tctctcacgc  cgcaaccatg   1020
acacatgcag gcatggcacc agaagcgcgt  gctgccgccg  ggatctccga  cgctgctg    1080
cgtatctcca ccggtattga agatggcgaa  gatttaattg  ccgacctgga  aaatggcttc   1140
cgggctgcaa acaagggggta a                                                  1161
```

<210> SEQ ID NO 8
<211> LENGTH: 5
<212> TYPE: PRT
<213> ORGANISM: Escherichia coli

<400> SEQUENCE: 8

Met Glu Thr Thr His
1               5

<210> SEQ ID NO 9
<211> LENGTH: 30
<212> TYPE: DNA
<213> ORGANISM: Artificial Sequence
<220> FEATURE:
<223> OTHER INFORMATION: MetJR

<400> SEQUENCE: 9
ggtacagaaa ccagcaggct gaggatcagc                                        30

<210> SEQ ID NO 10
<211> LENGTH: 100
<212> TYPE: DNA
<213> ORGANISM: Artificial Sequence
<220> FEATURE:
<223> OTHER INFORMATION: DmetJBF

<400> SEQUENCE: 10
tatgcagctg acgacctttc gcccctgcct gcgcaatcac actcattttt accccttgtt    60
tgcagcccgg aagccatttt caggcaccag agtaaacatt    100

<210> SEQ ID NO 11
<211> LENGTH: 30
<212> TYPE: DNA
<213> ORGANISM: Artificial Sequence
<220> FEATURE:
<223> OTHER INFORMATION: MetCR

<400> SEQUENCE: 11
cgtccgggac gccttgatcc cggacgcaac    30

<210> SEQ ID NO 12
<211> LENGTH: 32
<212> TYPE: DNA
<213> ORGANISM: Artificial Sequence
<220> FEATURE:
<223> OTHER INFORMATION: MetCF

<400> SEQUENCE: 12
gcgtttacgc agtaaaaaag tcaccagcac gc    32

<210> SEQ ID NO 13
<211> LENGTH: 100
<212> TYPE: DNA
<213> ORGANISM: Artificial Sequence
<220> FEATURE:
<223> OTHER INFORMATION: DmetCR

<400> SEQUENCE: 13
ccggcgtcca gatcggcaat cagatcgtcg acatcttcca gaccaatatg caggcgaatc    60
aaggtcccgc taaaatcgat catatgaata tcctccttag    100

<210> SEQ ID NO 14
<211> LENGTH: 100
<212> TYPE: DNA
<213> ORGANISM: Artificial Sequence
<220> FEATURE:
<223> OTHER INFORMATION: DmetCF

<400> SEQUENCE: 14
cggacaaaaa gcttgatact caactggtga atgcaggacg cagcaaaaaa tacactctcg    60
gcgcggtaaa tagcgtgatt tgtaggctgg agctgcttcg    100

<210> SEQ ID NO 15
<211> LENGTH: 100
<212> TYPE: DNA
<213> ORGANISM: Artificial Sequence
<220> FEATURE:
<223> OTHER INFORMATION: DcysKR

<400> SEQUENCE: 15
tgttgcaatt ctttctcagt gaagagatcg gcaaacaatg cggtgcttaa ataacgctca    60
cccgatgatg gtagaataac catatgaata tcctccttag    100

<210> SEQ ID NO 16
<211> LENGTH: 100
<212> TYPE: DNA
<213> ORGANISM: Artificial Sequence
<220> FEATURE:
<223> OTHER INFORMATION: DcysKF

```
<400> SEQUENCE: 16
agtaagattt tgaagataa ctcgctgact atcggtcaca cgccgctggt tcgcctgaat    60
cgcatcggta acggacgcat tgtaggctgg agctgcttcg                        100

<210> SEQ ID NO 17
<211> LENGTH: 100
<212> TYPE: DNA
<213> ORGANISM: Artificial Sequence
<220> FEATURE:
<223> OTHER INFORMATION: DcysMR

<400> SEQUENCE: 17
cccgccccct ggctaaaatg ctcttcccca aacaccccgg tagaaaggta gcgatcgcca    60
cgatcgcaga tgatcgccac catatgaata tcctccttag                        100

<210> SEQ ID NO 18
<211> LENGTH: 100
<212> TYPE: DNA
<213> ORGANISM: Artificial Sequence
<220> FEATURE:
<223> OTHER INFORMATION: DcysMF

<400> SEQUENCE: 18
agtacattag aacaaacaat aggcaatacg cctctggtga agttgcagcg aatggggccg    60
gataacggca gtgaagtgtg tgtaggctgg agctgcttcg                        100

<210> SEQ ID NO 19
<211> LENGTH: 30
<212> TYPE: DNA
<213> ORGANISM: Artificial Sequence
<220> FEATURE:
<223> OTHER INFORMATION: cysKR

<400> SEQUENCE: 19
tttttaacag acgcgacgca cgaagagcgc                                    30

<210> SEQ ID NO 20
<211> LENGTH: 30
<212> TYPE: DNA
<213> ORGANISM: Artificial Sequence
<220> FEATURE:
<223> OTHER INFORMATION: cysKR

<400> SEQUENCE: 20
ggcgcgacgg cgatgtgggt cgattgctat                                    30

<210> SEQ ID NO 21
<211> LENGTH: 30
<212> TYPE: DNA
<213> ORGANISM: Artificial Sequence
<220> FEATURE:
<223> OTHER INFORMATION: cysMR

<400> SEQUENCE: 21
ggggtgacgg tcaggactca ccaatacttc                                    30

<210> SEQ ID NO 22
<211> LENGTH: 30
<212> TYPE: DNA
<213> ORGANISM: Artificial Sequence
<220> FEATURE:
<223> OTHER INFORMATION: cysMF

<400> SEQUENCE: 22
```
gcgcgcatcg ctggccgctg ggctacacac                                     30

<210> SEQ ID NO 23
<211> LENGTH: 74
<212> TYPE: DNA
<213> ORGANISM: Artificial Sequence
<220> FEATURE:
<223> OTHER INFORMATION: MetYR

<400> SEQUENCE: 23
ttagagctgt tgacaattaa tcatccggct cgtataatgt gtggaataaa aactcttaag    60
gacctccaaa tgcc                                                     74

<210> SEQ ID NO 24
<211> LENGTH: 30
<212> TYPE: DNA
<213> ORGANISM: Artificial Sequence
<220> FEATURE:
<223> OTHER INFORMATION: MetYF

<400> SEQUENCE: 24
gctctgtcta gtctagtttg cattctcacg                                     30

<210> SEQ ID NO 25
<211> LENGTH: 100
<212> TYPE: DNA
<213> ORGANISM: Artificial Sequence
<220> FEATURE:
<223> OTHER INFORMATION: DudhAR

<400> SEQUENCE: 25
cccagaatct cttttgtttc ccgatggaac aaaattttca gcgtgcccac gttcatgccg    60
acgatttgtg cgcgtgccag tgtaggctgg agctgcttcg                         100

<210> SEQ ID NO 26
<211> LENGTH: 100
<212> TYPE: DNA
<213> ORGANISM: Artificial Sequence
<220> FEATURE:
<223> OTHER INFORMATION: DudhAF

<400> SEQUENCE: 26
ggtgcgcgcg tcgcagttat cgagcgttat caaaatgttg gcggcggttg cacccactgg    60
ggcaccatcc cgtcgaaagc catatgaata tcctccttag                         100

<210> SEQ ID NO 27
<211> LENGTH: 30
<212> TYPE: DNA
<213> ORGANISM: Artificial Sequence
<220> FEATURE:
<223> OTHER INFORMATION: UdhAR

<400> SEQUENCE: 27
gcgggatcac tttactgcca gcgctggctg                                     30

<210> SEQ ID NO 28
<211> LENGTH: 30
<212> TYPE: DNA
<213> ORGANISM: Artificial Sequence
<220> FEATURE:
<223> OTHER INFORMATION: UdhAF

<400> SEQUENCE: 28

```
ggccgctcag gatatagcca gataaatgac                                      30
```

<210> SEQ ID NO 29
<211> LENGTH: 100
<212> TYPE: DNA
<213> ORGANISM: Artificial Sequence
<220> FEATURE:
<223> OTHER INFORMATION: DpgiR

<400> SEQUENCE: 29

```
gcgccacgct ttatagcggt taatcagacc attggtcgag ctatcgtggc tgctgatttc      60
tttatcatct ttcagctctg catatgaata tcctccttag                           100
```

<210> SEQ ID NO 30
<211> LENGTH: 100
<212> TYPE: DNA
<213> ORGANISM: Artificial Sequence
<220> FEATURE:
<223> OTHER INFORMATION: DpgiF

<400> SEQUENCE: 30

```
ccaacgcaga ccgctgcctg gcaggcacta cagaaacact tcgatgaaat gaaagacgtt      60
acgatcgccg atcttttgc tgtaggctgg agctgcttcg                            100
```

<210> SEQ ID NO 31
<211> LENGTH: 30
<212> TYPE: DNA
<213> ORGANISM: Artificial Sequence
<220> FEATURE:
<223> OTHER INFORMATION: PgiR

<400> SEQUENCE: 31

```
cggtatgatt tccgttaaat tacagacaag                                      30
```

<210> SEQ ID NO 32
<211> LENGTH: 30
<212> TYPE: DNA
<213> ORGANISM: Artificial Sequence
<220> FEATURE:
<223> OTHER INFORMATION: PgiF

<400> SEQUENCE: 32

```
gcggggcggt tgtcaacgat ggggtcatgc                                      30
```

<210> SEQ ID NO 33
<211> LENGTH: 100
<212> TYPE: DNA
<213> ORGANISM: Artificial Sequence
<220> FEATURE:
<223> OTHER INFORMATION: DpfkAR

<400> SEQUENCE: 33

```
ttcgcgcagt ccagccagtc acctttgaac ggacgcttca tgttttcgat agcgtcgatg      60
atgtcgtggt gaaccagctg catatgaata tcctccttag                           100
```

<210> SEQ ID NO 34
<211> LENGTH: 100
<212> TYPE: DNA
<213> ORGANISM: Artificial Sequence
<220> FEATURE:
<223> OTHER INFORMATION: DpfkAF

<400> SEQUENCE: 34

```
ggtgtgttga caagcggcgg tgatgcgcca ggcatgaacg ccgcaattcg cggggttgtt      60
```

```
cgttctgcgc tgacagaagg tgtaggctgg agctgcttcg                          100
```

<210> SEQ ID NO 35
<211> LENGTH: 27
<212> TYPE: DNA
<213> ORGANISM: Artificial Sequence
<220> FEATURE:
<223> OTHER INFORMATION: PfkAR

<400> SEQUENCE: 35

```
ccctacgccc cacttgttca tcgcccg                                        27
```

<210> SEQ ID NO 36
<211> LENGTH: 27
<212> TYPE: DNA
<213> ORGANISM: Artificial Sequence
<220> FEATURE:
<223> OTHER INFORMATION: PfkAF

<400> SEQUENCE: 36

```
cgcacgcggc agtcagggcc gacccgc                                        27
```

<210> SEQ ID NO 37
<211> LENGTH: 100
<212> TYPE: DNA
<213> ORGANISM: Artificial Sequence
<220> FEATURE:
<223> OTHER INFORMATION: DpfkBR

<400> SEQUENCE: 37

```
gcgggaaagg taagcgtaaa tttttttgcgt atcgtcatgg gagcacagac gtgttccctg   60
attgagtgtg gctgcactcc catatgaata tcctccttag                          100
```

<210> SEQ ID NO 38
<211> LENGTH: 99
<212> TYPE: DNA
<213> ORGANISM: Artificial Sequence
<220> FEATURE:
<223> OTHER INFORMATION: DpfkBF

<400> SEQUENCE: 38

```
gcgccctctc tcgatagcgc aacaattacc ccgcaaattt atcccgaagg aaaactgcgc   60
tgtaccgcac cggtgttcgt gtaggctgga gctgcttcg                          99
```

<210> SEQ ID NO 39
<211> LENGTH: 26
<212> TYPE: DNA
<213> ORGANISM: Artificial Sequence
<220> FEATURE:
<223> OTHER INFORMATION: PfkBR

<400> SEQUENCE: 39

```
gccggttgca ctttgggtaa gccccg                                        26
```

<210> SEQ ID NO 40
<211> LENGTH: 30
<212> TYPE: DNA
<213> ORGANISM: Artificial Sequence
<220> FEATURE:
<223> OTHER INFORMATION: PfkBF

<400> SEQUENCE: 40

```
tggcaggatc atccatgaca gtaaaaacgg                                     30
```

```
<210> SEQ ID NO 41
<211> LENGTH: 29
<212> TYPE: DNA
<213> ORGANISM: Artificial Sequence
<220> FEATURE:
<223> OTHER INFORMATION: YveDR

<400> SEQUENCE: 41
cgtgaattct tattcatcaa ttctaataa                                          29

<210> SEQ ID NO 42
<211> LENGTH: 32
<212> TYPE: DNA
<213> ORGANISM: Artificial Sequence
<220> FEATURE:
<223> OTHER INFORMATION: YueDF

<400> SEQUENCE: 42
acgttcatga gatacgttat cataacagga ac                                      32
```

METHOD FOR THE PREPARATION OF AN EVOLVED MICROORGANISM FOR THE CREATION OR THE MODIFICATION OF METABOLIC PATHWAYS

This invention concerns a new method for the preparation of evolved microorganisms permitting the creation or modification of metabolic pathways, the strains of evolved microorganisms thereby obtained, the evolved genes coding for the evolved proteins that may be obtained by the method according to the invention, and the use of said evolved microorganisms, genes or proteins in a biotransformation process.

The preparation of microorganisms with modified properties is a widely used process. The aim is either to cause the microorganisms to evolve by letting them grow on a growth medium with a factor that exerts a selection pressure, so as to select those microorganisms able to resist that pressure, or to introduce one or more heterologous genes by means of widely used genetic engineering methods, in order to lend the microorganisms new phenotypic features associated with the expression of said heterologous gene or genes. This evolution can be favored by the use of mutagenic agents well known to those skilled in the art.

Methods for evolution by growth under selection pressure by removing a gene necessary for the transformation of a component of the culture medium, and by means of a mutagenic agent, are described in particular in FR 2 823 219 and WO 03/004656.

BRIEF DESCRIPTION OF THE INVENTION

This invention concerns a new method for the preparation of evolved microorganisms permitting the creation or modification of metabolic pathways, characterized in that it comprises the following steps:
   a) Modification of the cells of an initial microorganism so as to inhibit the production or consumption of a metabolite when that microorganism is grown on a defined medium, thereby adversely affecting the growth capacity of the microorganism. If the cells are not modified, the microorganism is able to produce or consume this metabolite, and displays a normal growth when it is grown on that same defined medium.
   b) Growth of the modified microorganism previously obtained on the said defined medium that caused it to evolve, where that defined medium can contain a co-substrate necessary for that evolution.
   c) Selection of the modified microorganism able to grow on the defined medium, with a co-substrate if appropriate.

The evolved microorganism preferentially contains at least one evolved gene coding for an evolved protein, the evolution of which makes it possible to replace the inhibited metabolic pathway by a new metabolic pathway.

This invention also concerns a method comprising an additional step a1) in which at least one heterologous gene coding for a heterologous protein is introduced, which heterologous gene is intended to cause the evolution of a new metabolic pathway, prior to step b) in which a modified microorganism is grown.

This invention also concerns a method comprising a step d) in which an evolved gene coding for said evolved protein is isolated.

This invention also concerns a method according to the invention whereby the evolved gene obtained previously is introduced, in an appropriate form, into a production microorganism intended for the production of the evolved protein.

This invention also concerns an evolved microorganism that may be obtained by a method according to the invention as defined above and below.

The invention also concerns a method for the preparation of an evolved protein characterized in that an evolved microorganism according to the invention is grown in an appropriate culture medium for the production of the evolved protein, which protein is purified when appropriate.

This invention also concerns an evolved gene coding for an evolved protein that may be obtained by a method according to the invention as defined above and below.

This invention also concerns an evolved protein that may be obtained by a method according to the invention as defined above and below.

This invention also concerns the use of an evolved microorganism or an evolved protein as defined above and below in a biotransformation process.

Definitions

According to the invention an 'evolved microorganism' is defined as a microorganism obtained by selection of a modified microorganism. The evolved microorganism displays at least one difference from the modified microorganism. This difference may, for example, be the improvement of an enzymatic characteristic, or the creation of a new metabolic pathway.

According to the invention a 'metabolic pathway' is one or more enzymatic reactions the succession of which forms a molecule (product) that is different from the starting molecule (substrate).

According to the invention a 'modification' is a change, in particular a deletion, of at least one gene and/or its promoter sequence, which gene codes for an enzyme.

According to the invention a 'metabolite' is a molecule synthesized and/or transformed by the microorganism.

According to the invention a 'defined medium' is a medium of known molecular composition suitable for the growth of the microorganism. The defined medium is substantially free of the metabolite or metabolites, the production of which is inhibited by performing the modification.

According to the invention a 'co-substrate' is an organic or inorganic molecule, different from the substrate, which is involved in a reaction and gives one or more of its atoms to the substrate to form a product. The co-substrate has no recognized mutagenic properties.

According to the invention 'selection' is a culture method used to select microorganisms that have evolved in such a way that a modification does not affect growth. A preferred application is a continuous culture method, carried out by applying increasing rates of dilution so as to conserve in the culture medium only those microorganisms with a growth rate equal to or greater than the imposed rate of dilution.

According to the invention an 'evolved gene' is a sequence of nucleic acids (comprising A, T, G or C) bounded by a stop codon (TAA, TAG, TGA) in phase and possessing, after selection, at least one nucleic acid that is different from the initial sequence, so that the protein coded by that evolved gene differs in at least one amino acid from the protein coded by the initial gene.

According to the invention a 'heterologous gene' is a sequence of nucleic acids bounded by a start codon (ATG or GTG) and a stop codon (TAA, TAG, TGA) in phase, called a coding sequence, derived from an organism different from that used to carry out the evolution and/or the production.

According to the invention an 'evolved protein' is a sequence of amino acids (protein sequence) that differs in at least one amino acid from the initial protein sequence after selection.

According to the invention a 'heterologous protein' is a protein resulting from the translation of a heterologous gene.

The genes and proteins can be identified by their primary sequences, but also by sequence or alignment homology defining groups of proteins.

PFAM (protein families database of alignments and hidden Markov models represents a large collection of protein sequence alignments. Each PFAM makes it possible to visualize multiple alignments, see protein domains, evaluate distribution among organisms, gain access to other databases, and visualize known protein structures.

COGs (clusters of orthologous groups of proteins are obtained by comparing protein sequences from 43 fully sequenced genomes representing 30 major phylogenic lines. Each COG is defined from at least three lines, which permits the identification of former conserved domains.

The means of identifying homologous sequences and their percentage homologies are well known to those skilled in the art, and include in particular the BLAST programs with the default parameters indicated on that website. The sequences obtained can then be exploited (e.g., aligned) using, for example, the programs CLUSTALW or MULTALIN with the default parameters indicated on those websites.

Using the references given on GenBank for known genes, those skilled in the art are able to determine the equivalent genes in other organisms, bacterial strains, yeasts, fungi, mammals, plants, etc. This routine work is advantageously done using consensus sequences that can be determined by carrying out sequence alignments with genes derived from other microorganisms, and designing degenerate probes to clone the corresponding gene in another organism. These routine methods of molecular biology are well known to those skilled in the art, and are described, for example, in Sambrook et al. (1989 Molecular Cloning: a Laboratory Manual. $2^{nd}$ ed. Cold Spring Harbor Lab., Cold Spring Harbor, N.Y.).

The genes that may be deleted or overexpressed for the evolved strains according to the invention are principally defined using the denomination of the gene of *E. coli*. However, this usage has a more general meaning according to the invention and covers the corresponding genes of other microorganisms. Using the GenBank references for the genes of *E. coli* those skilled in the art can determine the equivalent genes in bacterial strains other than *E. coli*.

According to the invention a 'new metabolic pathway' is a set of one or more enzyme reactions, the succession of which produces a chemical entity, that, after the step to select the evolved microorganism, differs in its enzymatic activities from the corresponding pathway in the corresponding non-evolved microorganism. This difference can reside in the type of reaction catalyzed, or in kinetic characteristics ($K_m$, $V_{max}$, $K_i$, etc.). A new enzymatic pathway makes it possible to produce a chemical entity different from or the same as the initial product, from a substrate different from or the same as the initial substrate.

According to the invention an 'appropriate form' is a sequence of nucleic acids, bounded by a start codon (ATG or GTG) and a stop codon (TAA, TAG, TGA) in phase, called a coding sequence, or a part of that coding sequence, under the control of regulators necessary for its expression in the microorganism in which the heterologous gene is to be expressed. These regulators are well known to those skilled in the art, and include promoting regulators, or promoters, in particular promoters called strong constitutive promoters in microorganisms. The constitutive promoter is preferably chosen from among pTAC-O, pLAC-O, pTRC-O, strong promoters for which the lac operator has been deleted to make them constitutive, pTHLA.

According to the invention an 'initial microorganism' is a microorganism that has not yet undergone any modification, mutation or evolution.

According to the invention a 'production microorganism' is an evolved microorganism or optimized microorganism into which a new metabolic pathway from an evolved microorganism has been introduced.

According to the invention a 'modified microorganism' is a microorganism obtained by performing controlled modifications, i.e., that are not the result of a process of evolution. Examples of such a modification are the directed mutation or deletion of a gene, or the directed modification of a promoter.

According to the invention a 'culture medium suitable for the production of the evolved protein' is a medium of defined composition, or a complex medium, or a partially defined medium. The complex medium is obtained from a plant, microorganism or animal hydrolysate; its composition may be determined by analysis, although an exhaustive analysis of this type of medium is seldom possible. A partially defined medium is a defined medium to which a complex medium has been added.

According to the invention a 'biotransformation process' is a process whereby a molecule A is transformed into a molecule B by means of one or more enzymes, which may or may not be contained in one or more microorganisms. There are three types of biotransformation: bioconversion, fermentation and biocatalysis. In bioconversion, the enzyme or enzymes are produced in one or more microorganisms grown on a suitable medium, and substance A and if necessary one or more co-substrates are supplied for conversion into substance B. In fermentation, the enzyme or enzymes are produced in one or more microorganisms grown on a suitable medium to enable the microorganism or microorganisms to synthesize substance A; the suitable medium can contain co-substrates. In biocatalysis, the enzyme or enzymes are not in cells but in a suitable medium supplying substance A and any co-substrates necessary for the biotransformation.

The methods for the isolation of genes are well known to those skilled in the art, and are described in particular in Sambrook et al. (1989 Molecular Cloning: a Laboratory Manual. $2^{nd}$ Ed. Cold Spring Harbor Lab., Cold Spring Harbor, N.Y.), Ausubel et al., 1987 (Current Protocols in Molecular Biology, John Wiley and Sons, New York); Maniatis et al., 1982, (Molecular Cloning: a Laboratory Manual. Cold Spring Harbor Laboratory, Cold Spring Harbor, N.Y.). These methods make it possible to locate, copy or extract the gene in order to introduce it into a new organism. This last step can be preceded by a step in which the gene is incorporated into a polynucleotide before being introduced into the microorganism.

Methods for purifying proteins are well known to those skilled in the art, and are described in particular in Coligan et al., 1997 (Current Protocols in Protein Science, John Wiley & Sons, Inc). They make it possible to identify a protein of interest in a fractionated or non-fractionated protein extract. This protein can then be purified, resulting in an increase in its specific activity if it is an enzyme. Lastly, these methods make it possible, if necessary, to immobilize the protein on a support (e.g., a resin).

According to the invention a 'deletion' is the suppression of the activity of the 'deleted' gene. This suppression can result from an inactivation, by suitable means, of the product of the expression of the gene concerned, or the inhibition of the expression of the gene concerned, or the deletion of at least part of the gene concerned so that its expression is impaired (for example deletion of part or all of promoter region necessary for its expression), or the loss of function of the product of the expression (for example deletion in the coding part of the gene concerned). The deletion of a gene preferably consists of the removal of most of that gene, and if appropriate its replacement by a selection marker gene to facilitate identification, isolation and purification of the evolved strains according to the invention.

According to the invention a 'substrate' is a metabolite that can be transformed by the action of an enzyme, if necessary in the presence of a co-substrate.

DETAILED DESCRIPTION OF THE INVENTION

A. Modified Microorganisms

The strains of modified microorganisms according to the invention can be prokaryotic or eukaryotic.

According to the invention a strain of a microorganism is a set of microorganisms belonging to the same species, that comprises at least one microorganism of that species. Thus the characteristics described for the strain apply to each of the microorganisms of that strain. Likewise, the characteristics described for one of the microorganisms of the strain apply to all the microorganisms of which that strain is composed.

The optimized bacteria according to the invention are selected from among bacteria, yeasts and fungi, in particular among the following species: *Aspergillus* sp., *Bacillus* sp., *Brevibacterium* sp., *Clostridium* sp., *Corynebacterium* sp., *Escherichia* sp., *Gluconobacter* sp., *Pseudomonas* sp., *Rhodococcus* sp., *Saccharomyces* sp., *Streptomyces* sp., *Xanthomonas* sp., *Candida* sp.

In a preferred embodiment the bacterial strain is a strain of *Escherichia*, in particular *E. coli*. In another embodiment the bacterial strain is a strain of *Corynebacterium*, in particular *C. glutamicum*.

In another embodiment the yeast strain is a strain of *Saccharomyces*, in particular *S. cerevisiae*

To prepare such modified microorganisms it can be advantageous to attenuate, and in particular to delete, other genes associated with or independent of the metabolic pathway to be modified, in order to favor the evolution of the microorganism.

To prepare such modified microorganisms it can also be advantageous to favor, and in particular to overexpress, other heterologous or non-heterologous genes, associated with or independent of the metabolic pathway to be modified, in order to favor the evolution of the microorganism.

The overexpression of a gene can be achieved by replacing the promoter of that gene in situ by a strong or inducible promoter. Alternatively, a single-copy or multicopy replicative plasmid in which the gene that is to be overexpressed is controlled by the appropriate promoter is introduced into the cell.

Such modifications will be decided on case by case according to the choice of metabolic pathway to be modified. In particular they will be described case by case for the particular metabolic pathways outlined below.

Those skilled in the art know the protocols used to modify the genetic characters of microorganisms.

The inactivation of a gene is carried out preferably by homologous recombination. (Datsenko, K. A.; Wanner, B. L. (2000), One-step inactivation of chromosomal genes in *Escherichia coli* K-12 using PCR products. *Proc. Natl. Acad. Sci. USA* 97: 6640-6645). The principal of a protocol is briefly as follows: a linear fragment obtained in vitro is introduced into the cell; this fragment comprises the two regions flanking the gene and at least one gene of selection between these two regions (generally a gene of resistance to an antibiotic); the fragment therefore presents an inactivated gene. The cells that have undergone a recombination event and have integrated the fragment are then selected by spreading them on a selective medium. The cells that have undergone a double recombination event in which the native gene has been replaced by the inactivated gene are then selected. This protocol can be improved by using positive or negative selection systems to increase the rate of detection of double recombination events.

The inactivation of a gene in *S. cerevisiae* is achieved preferably by homologous recombination (Baudin et al., *Nucl. Acids Res.* 21, 3329-3330, 1993; Wach et al., *Yeast* 10, 1793-1808, 1994; Brachmann et al., *Yeast.* 14:115-32, 1998).

B. Production Microorganisms

The production microorganisms are also selected from among the bacteria, yeasts and fungi listed above. They can be evolved microorganisms obtained by the evolution procedure according to the invention, or microorganisms optimized for the production of a desired metabolite, in which at least one evolved gene according to the invention has been introduced.

C. Culture of Microorganisms

According to the invention, the terms 'culture' and 'fermentation' are used indifferently to denote the growth of a microorganism on an appropriate culture medium containing a simple carbon source.

According to the invention a simple carbon source is a source of carbon that can be used by those skilled in the art to obtain normal growth of a microorganism, in particular of a bacterium. In particular it can be an assimilatable sugar such as glucose, galactose, sucrose, lactose or molasses, or by-products of these sugars. An especially preferred simple carbon source is glucose. Another preferred simple carbon source is sucrose.

Those skilled in the art are able to define the culture conditions for the microorganisms according to the invention. In particular the bacteria are fermented at a temperature between 20° C. and 55° C., preferably between 25° C. and 40° C., and more specifically about 30° C. for *C. glutamicum* and about 37° C. for *E. coli*.

The fermentation is generally conducted in fermenters with an inorganic culture medium of known defined composition adapted to the bacteria used, containing at least one simple carbon source, and if necessary a co-substrate necessary for the production of the metabolite.

In particular, the inorganic culture medium for *E. coli* can thus be of identical or similar composition to an M9 medium (Anderson, 1946, *Proc. Natl. Acad. Sci. USA* 32:120-128), an M63 medium (Miller, 1992; A Short Course in Bacterial Genetics: A Laboratory Manual and Handbook for *Escherichia coli* and Related Bacteria, Cold Spring Harbor Laboratory Press, Cold Spring Harbor, N.Y.) or a medium such as that defined by Schaefer et al. (1999, *Anal. Biochem.* 270: 88-96).

Analogously, the inorganic culture medium for *C. glutamicum* can thus be of identical or similar composition to BMCG medium (Liebl et al., 1989, *Appl. Microbiol. Biotechnol.* 32: 205-210) or to a medium such as that described by Riedel et al. (2001, *J. Mol. Microbiol. Biotechnol.* 3: 573-583).

D. Metabolic Pathways

The metabolic pathways to be evolved are generally selected from among the synthetic pathways of amino acids, the synthetic pathways of nucleic acids, the synthetic pathways of lipids or the metabolic pathways of sugars.

In a first preferred embodiment of the invention, the evolved metabolic pathway is a biosynthesis pathway of amino acids, in particular a biosynthesis pathway of an amino acid selected from among methionine, cysteine, threonine, lysine, or isoleucine.

In a second preferred embodiment of the invention the modified metabolic pathway is a pathway by which NADP is regenerated from NADPH. In particular the biosynthesis pathway of cysteine, of hydroxypropionate and of xylitol will be cited.

D.I. The Methionine Biosynthesis Pathway

The invention can be applied, for example, to the methionine biosynthesis pathway (FIG. 1) and yields strains of microorganisms, in particular bacteria, e.g., *E. coli* and corynebacteria, that produce methionine by metabolism of a simple carbon source and a sulfur source, in particular methylmercaptan ($CH_3SH$), hydrogen sulfide ($H_2S$) or physiologically acceptable salts of these. The sulfur source $H_2S$ can also be introduced into the culture medium as sulfate.

According to the invention a 'physiologically acceptable salt' is one that does not affect the metabolism or ability to grow of the strain of microorganism according to the invention, in particular the salts of alkali metals such as sodium.

The use of a simple carbon source and a sulfur compound, in particular methylmercaptan or hydrogen sulfide for the production of methionine by bioconversion can be expected to offer certain advantages:

The synthesis of methionine in one or two steps from O-acyl-L-homoserine becomes independent of the synthesis of cysteine and also of the tetrahydrofolate cycle;

Sulfur compounds such as methylmercaptan, generally toxic raw materials derived from the petrochemical industry, can be put to good use for the synthesis of amino acids with high added value.

The invention is based on the fact that it is possible to obtain, in a controlled manner, a modification of the 'methionine-synthase' activity of cystationine-γ-synthase (EC 4.2.99.9; GenBank AAN83320, or AAA24167) in the presence of methylmercaptan. This enzyme of the methionine biosynthesis pathway, coded for by the gene metB in *E. coli* (FIG. 2) and *C. glutamicum*, displays an activity for a wide range of substrates (Flavin, M.; Slaughter, C. (1967), Enzymatic synthesis of homoserine or methionine directly from O-succinyl-homoserine. *Biochim Biophys. Acta* 132: 400-405).

The invention is also based on the fact that it is possible to obtain, in a controlled manner, a modification of the 'methionine-synthase' activity of O-acetyl-L-homoserine sulfhydrolase (or O-acetyl-L-homoserine sulfhydrylase, C 4.2.99.10) in the presence of methylmercaptan. This enzyme of the methionine biosynthesis pathway, coded for by the gene metY (FIG. 2) in *C. glutamicum* (Genbank AF220150), displays an activity for a wide range of substrates (Smith I K, Thompson J F. (1969), Utilization of S-methylcysteine and methylmercaptan by methionineless mutants of Neurospora and the pathway of their conversion to methionine. II. Enzyme studies. *Biochim Biophys Acta* 184(1): 130-8).

The application of the invention to the modification of the biosynthesis pathway of methionine requires first genetically modifying the initial bacterium. This modification necessarily involves the attenuation of at least one gene and possibly the cloning of at least one heterologous gene. The attenuation of the gene must make the bacterium depend on the restoration of an equivalent metabolic pathway to allow it to grow. The genetically modified bacterium is grown, and the bacterial strain or strains whose growth improves in the presence or absence of an exogenous co-substrate are selected.

In a preferred embodiment of the invention, this modification of the initial strain, in particular *E. coli*, consists in inactivating the native methionine-synthase activity (coded for by the gene metE in *E. coli*), and then growing the resulting modified microorganisms on a defined medium containing no methionine, S-adenosylmethionine, homocysteine or cystathionine, but containing methylmercaptan (exogenous co-substrate), or one of its salts, and selecting an evolved microorganism characterized in that the methionine-synthase activity of cystathionine γ-synthase is strongly improved, in the presence of methylmercaptan, replacing the initially suppressed activity. In this embodiment of the invention it is important to note that the medium used to select the evolved microorganism is identical to the medium on which the initial (i.e., unmodified) microorganism grew; only a co-substrate (e.g., methylmercaptan) is added. According to a preferred embodiment of the invention the selected bacterial strain comprising the evolved microorganism according to the invention is a strain of *E. coli*, preferentially the strain *E. coli* K183, registered under the number 1-3005, on Apr. 2 2003 in the Collection Nationale de Culture et Microorganismes (CNCM), 25 rue du Docteur-Roux, 75724 Paris Cedex 15, France, in accordance with the provisions of the Treaty of Budapest. This strain comprises a gene expressing a modified cystathionine-γ-synthase, the enzyme containing the mutation E325A, and an inactivation of the gene metE. In a particular embodiment of this invention it is also possible to use strains with additional metC and/or metH and/or metJ deletions.

In a second equally preferred embodiment of the invention, the stated modification of the initial strain, in particular *E. coli*, consists in suppressing the activity of cystathionine-β-lyase (coded for by the gene metC in *E. coli*) and growing the resulting modified microorganism on a medium containing no methionine, S-adenosylmethionine, homocysteine or cystathionine, and then selecting an evolved microorganism characterized in that the homocysteine-synthase activity of the cystathionine γ-synthase is strongly improved in the presence of endogenous $H_2S$, replacing the initially suppressed activity. In this embodiment of the invention it is important to note that the medium used to select the evolved microorganism is identical to the medium on which the initial (i.e., unmodified) microorganism grew. In a particular embodiment it is also possible to add NaSH to the medium. In another embodiment it is possible to use a strain that additionally presents at least one mutation in metH and/or metJ.

In a third equally preferred embodiment of the invention the stated modification of the initial microorganism, in particular *E. coli*, consists in suppressing the native cystathionine-γ-synthase activities (coded for by the gene metB) and methionine-synthase activities (coded for by the gene metE in *E. coli*), and then introducing the acetyl-homoserine sulfhydrylase activity (coded for by the gene metY of *C. glutamicum*), and growing the resulting modified microorganism on a defined medium containing no methionine, S-adenosylmethionine, homocysteine or cystathionine, but supplemented with sodium methylmercaptide in order to select an evolved microorganism characterized in that the methionine-synthase activity exhibited by the acetyl-homoserine sulfhydrylase (METY) is strongly improved, in the presence of sodium methylmercaptide, replacing the initially suppressed methionine-synthase activity. In this embodiment of the invention it is important to note that the medium used to select the evolved microorganism is identical to the medium on which the initial (i.e., unmodified) microorganism grew; only a co-substrate (e.g., methylmercaptan) is added. In a particular embodiment it is possible to use a strain that additionally presents at least one mutation in metH and/or metJ and/or metC.

The procedure for preparing strains according to the invention consists in obtaining, from an initial bacterial strain, a genetically modified bacterial strain presenting at least one modification in a gene coding for an enzyme with a 'methionine synthase' (e.g. MetE) or 'homocysteine synthase' (e.g. MetC) activity, by a process comprising a step in which the initial bacterial strain is subjected to selection pressure in the presence of the sulfur source specified above, in order to cause the evolution of at least one gene (e.g., metB) in that bacterial strain, so as to restore a 'methionine synthase' or 'homocysteine synthase' activity in the evolved strain, this restoration of activity not being due to a reversal of the modification made.

A 'methionine-synthase' or 'homocysteine-synthase' activity is improved in the evolved microorganism strain (E) compared with that of the modified strain (M) when the production of methionine in the same culture conditions (in a medium containing an efficient quantity of methylmercaptan) is greater in strain E than in strain M. This improvement is preferably observed by measuring the quantity of methionine produced. In some cases this improvement can be observed by the increase in the growth rate of strain E compared with that of strain M in a minimal medium containing no methionine.

Those skilled in the art will be able to identify other genes coding for enzyme activities that can evolve into 'methionine synthase' or 'homocysteine synthase' activities, and will be able accordingly to adapt the modifications to be made to the initial microorganism before selecting it. One example is cysteine synthases A and B coded for by genes cysK and cysM in bacteria.

For modified cystathionine-γ-synthases defined above and below, the substrate is advantageously O-acetyl-L-homoserine or O-succinyl-L-homoserine, and preferably O-succinyl-L-homoserine.

For modified acylhomoserine sulfhydrylases defined above and below, the substrate is advantageously O-succinyl-L-homoserine or O-acetyl-L-homoserine, and preferably O-acetyl-L-homoserine.

For these two enzymes the modification consists of a mutation such that methylmercaptan or hydrogen sulfide is preferred to L-cysteine.

In a particular embodiment of the invention, the sequence coding for cystathionine-γ-synthase or acylhomoserine sulfhydrylase is:
  either a native gene present in the genome of the initial strain (I) in which it is expressed to permit the translation of the corresponding enzyme,
  or a heterologous gene comprising a sequence coding for a cystathionine-γ-synthase or an acylhomoserine sulfhydrylase, under the control of regulators that permit its expression and transduction in the modified strain (M) into which it is to be introduced.

Heterologous cystathionine-γ-synthases are advantageously selected from among the cystathionine-γ-synthases corresponding to PFAM reference PF01053 and COG reference CPG0626.

In a preferred embodiment the modified bacterial strain presents an inactivation of at least one endogenous gene selected from among metB, metJ, metC, metE, and metH.

A mutation of the gene metJ was proposed in JP 2000157267-A/3, to produce a greater quantity of methionine (see also GenBank E35587). This gene codes for a repressor protein for genes met B, E, L, J and R (in *Salmonella typhimurium*). Its inactivation or modification reduces the feedback regulation by methionine.

The gene metC (GenBank M12858) codes for cystathionine-β-lyase (EC 4.4.1.8), the genes metE (GenBank AE000458) and metH (GenBank J04975) code for methionine synthase (EC 2.1.1.13). Methionine is an amino acid that is essential for cell viability. The effect of inactivating one or more of these genes is to close the usual methionine synthesis pathway.

A further object of the invention is thus a method for the evolution and selection of a modified bacterial strain that possesses a gene coding for the enzymes cystathionine-γ-synthase or acylhomoserine sulfhydrylase, for the purpose of obtaining a genetically modified bacterial strain that produces an amino acid of formula (I), $$R\text{—}S\text{—}(CH_2)_2\text{—}CHNH_2\text{—}COOH \quad (I)$$

in particular L-methionine, and presenting a modification in the gene of that enzyme that induces a modification of the 'methionine synthase' activity in the presence of a sulfur compound defined previously. The method involves the step that consists in subjecting the said bacterial strain to a selection pressure in the presence of the said sulfur compound, in order to cause an evolution of the gene coding for the enzyme cystathionine-γ-synthase or acylhomoserine sulfhydrylase in the said bacterial strain, which evolution consists in at least one mutation that preferably permits the direct conversion of the substrate into methionine or homocysteine.

The said initial bacterial strain may present an inactivation and/or overactivation, in particular by insertion of a strong constitutive promoter, of at least one endogenous gene.

The invention further concerns a bacterial strain presenting a modification to the gene of the enzyme cystathionine-γ-synthase and/or the gene of the enzyme acylhomoserine sulfhydrylase, inducing an increase in the 'methionine synthase' activity of that enzyme in the presence of the sulfur compound, in particular methylmercaptan. Such a strain can also present at least one further genetic modification, (inactivation, mutation or overexpression of an endogenous gene), as stated above.

The strain according to the invention can preferably be obtained by a method according to the invention, and in particular is obtained by the method according to the invention.

The invention further concerns a method for the preparation of methionine, in which a microorganism is grown that has a modified 'methionine synthase' activity as defined previously, in the presence of a sulfur compound in an appropriate medium, which appropriate medium contains a simple carbon source as defined previously. The methionine is preferably L-methionine, and the sulfur compound present is preferably methylmercaptan or $H_2S$.

The media can be supplemented to compensate for auxotrophies other than that caused by the deletion of the genes metE and/or metC and/or metB; they contain a simple carbon source at a concentration appropriate to the mode of culture and of production, and a sulfur compound at a concentration appropriate to the evolution of the strain and to the desired mode of production.

After fermentation the methionine is recovered by the usual methods and purified if necessary.

The methods for the recovery and subsequent purification of the methionine in the culture media are well known to those skilled in the art.

This invention further concerns a method for the preparation of methionine in which a derived substrate of general formula (III)

$$R''\text{—}O\text{—}(CH_2)_2\text{—}CHNH_2\text{—}COOH \quad (III)$$

where R" is an acyl radical, preferably either the succinyl radical or the acetyl radical, is made to react with an enzyme with an evolved 'methionine synthase' activity as defined previously, in an appropriate reaction medium containing a sulfur compound defined previously.

The appropriate reaction medium is a usual enzymatic reaction medium, well known to those skilled in the art, in particular an aqueous medium in which the substrates and the enzyme are dissolved or suspended. The conditions in which the reaction is carried out are well known to those skilled in the art, in particular those conditions designed to prevent substantial denaturing of the enzymes.

In a particular embodiment of the invention, the enzyme with evolved 'methionine synthase' activity is present in an inactivated bacterium or in a cell extract.

In another particular embodiment of the invention the enzyme with evolved 'methionine synthase' activity is a purified enzyme.

D.II. The Cysteine Biosynthesis Pathway

The invention can also be applied, for example, to the cysteine biosynthesis pathway (FIG. 3) providing strains of evolved microorganisms, in particular bacteria, e.g., *E. coli* and corynebacteria, that produce 2-amino-4-(alkylmercapto) propionic acids with the general formula (I)

$$R\text{—}S\text{—}CH_2\text{—}CHNH_2\text{—}COOH \quad (I)$$

where R is a straight-chain or branched-chain alkyl radical with 1 to 18 carbon atoms, that may bear one or more hydroxy substituents, or an aryl radical, or a heteroaryl radical containing one or more nitrogen or sulfur atoms in the heteroaromatic ring, selected from among the phenyl, pyridyl, pyrolyl, pyrazolyl triazolyl, tetrazolyl, thiazolyl, and thienyl groups, by the metabolism of a simple carbon source and a source of sulfur consisting of a compound of general formula (II):

$$R'\text{—}SH \quad (II)$$

where R' is a hydrogen atom or R, R being defined above, and its physiologically acceptable salts, which strains present at least one gene coding for a mutated enzyme with an 'evolved cysteine synthase' activity.

According to the invention a 'physiologically acceptable salt' of the compound of general formula (I) is one that does not effect the metabolism or ability to grow of the microorganism strain according to the invention, in particular the salts of alkali metals such as sodium.

In a preferred embodiment of the invention, R is a straight-chain or branched-chain alkyl radical containing 1 to 4 atoms of carbon, selected in particular from among the methyl, ethyl, n-propyl, i-propyl, n-butyl, i-butyl and t-butyl groups. R is preferentially a methyl radical.

The 2-amino-4-(alkylmercapto)propionic acid of general formula (I) obtained is preferably L-cysteine.

According to the invention an enzyme with evolved 'cysteine synthase' activity is any mutated enzyme involved in the biosynthesis of the amino acid of general formula (I), in particular L-cysteine, the essential activity of which is to carry out the direct conversion of an acetylserine, preferably O-acetyl-L-serine, into an amino acid of general formula (I) in the presence of a sulfur compound of general formula (II), whereas the essential activity of the initial non-mutated enzyme was not a 'cysteine synthase' activity. The enzymes naturally involved in the biosynthesis of cysteine by the direct conversion of O-actetyl-L-serine (acetylserine) into L-cysteine in the presence of hydrogen sulfide (H$_2$S), such as cysteine synthases A and B, coded for by genes cysK or cysM, respectively, are therefore excluded from this definition.

The 'initial' non-mutated enzyme is preferentially an enzyme that catalyzes a sulfhydrylation reaction in the presence of H$_2$S, preferably an enzyme with O-acyl-L-homoserine sulfhydrolase activity.

The 'initial' enzymes with O-acyl-L-homoserine sulfhydrylase activity are advantageously selected form among the O-acyl-L-homoserine sulfhydrylases corresponding to PFAM reference PF01053 and COG reference COG2873.

The O-acyl-L-homoserine sulfhydrolase is preferentially selected from among the O-acyl-L-homoserine sulfhydrolases coded for by the gene metY of corynebacterium, in particular the gene metY of *C. glutamicum* (Genbank AF220150), and the homologous enzymes presenting the same O-acyl-L-homoserine sulfhydrolase activity, and at least 80% sequence homology with O-acyl-L-homoserine sulthydrolase coded for by the gene metY of *C. glutamicum* (Genbank AF220150), preferably at least 85% homology, and more preferably at least 90% homology.

The invention is in particular based on the fact that it is possible to obtain, in a controlled manner, a modification of the substrate specificity of the enzyme acyl-homoserine sulfhydrylase so that it uses acetylserine preferentially. Consequently the invention is based on the fact that it is possible to modify, in a controlled manner, the substrate specificity of the unmodified enzyme in order to evolve from an acylhomoserine sulfhydrolase activity to a cysteine synthase activity.

In a preferred embodiment of the invention, the strains of unmodified microorganisms do not naturally possess O-acyl-L-homoserine sulfhydrolase activity or do not possess a gene homologous to the gene metY that codes for that enzyme.

The strains modified according to the invention are genetically modified by the inactivation, mutation and/or overactivation of at least one endogenous gene in order to permit the evolution of a new metabolic pathway. In particular, the strains of microorganisms according to the invention are genetically modified to suppress the genes cysK and/or cysM coding for the proteins respectively bearing the cysteine synthase A, and cysteine synthase B enzyme activities. The genes cysK and cysM are preferentially suppressed.

The gene cysK (FIG. 4) codes for cysteine synthase A (GenBank NP_416909) and the gene cysM codes for Icystene synthase B (GenBank NP_416916). The effect of inactivating these genes closes the cysteine biosynthesis pathways and so makes the strain auxotrophic for cysteine.

A gene is then introduced into the modified bacteria that codes for an enzyme catalyzing a sulfhydrylation reaction in the presence of H$_2$S, as defined previously, other than those enzymes the main activity of which is a cysteine synthase activity (also called O-acetylserine sulfhydrolase), in particular a gene coding for an O-acyl-L-homoserine sulfhydrolase, such as the gene metY of *Corynebacterium*, and in particular the gene metY of *C. glutamicum* (Genbank AF220150).

The gene coding for an enzyme catalyzing a sulfhydrylation reaction in the presence of H$_2$S can be introduced into the bacterium to be modified by the usual methods available to those skilled in the art, either by direct integration or carried by a replicative plasmid.

The strain modified in this way is preferably selected and improved by a method of screening and evolution, which is also an object of this invention, and which makes it possible to cause the acyl-homoserine sulfhydrylase activity to evolve into a cysteine synthase activity to restore the production of cysteine.

The transformation of the acyl-homoserine sulfhydrylase activity into an 'evolved cysteine synthase' activity is deemed to be achieved when the genetically modified and evolved bacterial strain (E) has a growth rate at least similar to that of the initial modified strain (M) when grown in a minimal medium in the presence of glucose as a single carbon source. In a particular embodiment the transformation of the acyl-homoserine sulfhydrylase activity into the 'evolved cysteine synthase' activity is deemed to be achieved when the cysteine synthase activity carried by the modified O-acyl-L-homoserine sulfhydrolase protein has been improved by 10% relative to its initial activity. In some cases this improvement can be observed by an increased growth rate of bacterium E relative to that of bacterium M. Lastly, this transformation of the acyl-homoserine sulfhydrylase activity into an 'evolved cysteine synthase' activity will be deemed achieved when strain E produces at least as much cysteine as strain M in equivalent culture conditions, in the absence of any initial cysteine content.

The strains according to the invention can also be genetically modified by inactivation, mutation and/or overactivation of at least one endogenous gene, such modification being made before or after the evolution step of the modified strain. The metB coding for cystathionine y-synthase activity can be altered if required.

The gene coding for cystathionine gamma-lyase activity can be deleted, if required.

In one embodiment the bacterial strain can also undergo modification of the serine O-acyltransferase activity carried by the gene cysE (FIG. 4) to make it insensitive to feedback inhibition by cysteine.

In another embodiment the bacterial strain can also be made to overexpress the gene cysB in order to deregulate the $H_2S$ sulfur assimilation pathway.

Figure 4:
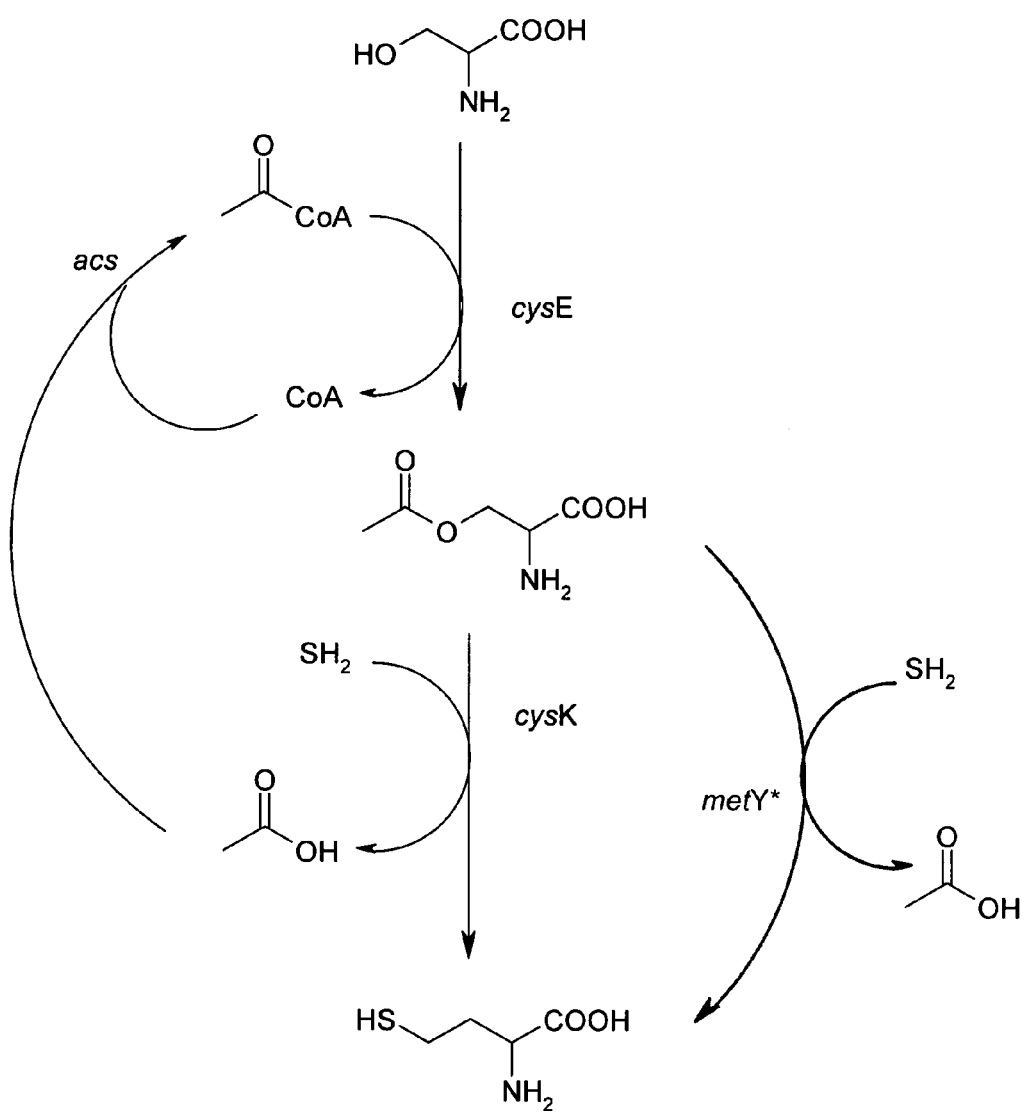

It can also be advantageous for the production of amino acids of formula (I), preferably L-cysteine, to overexpress the gene coding for acetyl-CoA synthetase, such as the gene acs (EC 6.2.1.1), accession number AE000480, at the same time as the gene coding for an enzyme with an 'improved cysteine synthase activity' defined previously (FIG. 4).

It can also be advantageous to attenuate or even delete genes coding for an acetate kinase and/or for a phosphotransacetylase, in particular the genes ack and pta accession numbers AE000318 and AE000319 respectively, and coding respectively for an acetate kinase (EC 2.7.2.1) and a phosphotransacetylase (EC 2.3.1.8). This attenuation/deletion is preferably combined with an overexprssion of the gene coding for acetyl-CoA synthetase.

All the modifications stated above can be made on the modified strain before the process of evolution of the gene metY or on the evolved strain, that is after the evolution of the gene metY, but not for deletions of cysK and/or cysM, which have to be carried out before the process of growth and evolution of the modified strain.

The invention thus further concerns a method for the preparation of a bacterial strain with an 'evolved cysteine synthase activity' as defined previously, which method comprises a step consisting in growing, in an appropriate culture medium containing a simple carbon source, a bacterial strain possessing an enzyme catalyzing a sulfhydrylation reaction in the presence of $H_2S$ of which the essential activity is not a 'cysteine synthase' activity as defined previously, in order to cause an evolution of the gene coding for that enzyme in that bacterial strain into a gene coding for an 'evolved cysteine synthase' activity.

The invention further concerns a method for the preparation of cysteine, in which a microorganism with an 'evolved cysteine synthase' activity as defined previously is grown in an appropriate culture medium containing a simple carbon source as defined previously.

The definition of the fermentation conditions belongs to those skilled in the art. The fermentation is conducted in fermenters with an inorganic growth medium of known set composition adapted according to the bacteria used, containing at least one simple carbon source.

The media can be supplemented to compensate for the auxotrophies other than that caused by the deletion of the genes cysK and/or cysM; they contain a simple source of carbon at a concentration adapted according to the mode of growth and production, and a sulfur compound of formula (II) at a concentration adapted according to the evolution of the strain and to the desired mode of production.

After fermentation, the cysteine is recovered by the usual methods and purified if necessary.

The methods of recovery and purification of cysteine in culture media are well known to those skilled in the art.

This invention further concerns a method for the preparation of an amino acid of general formula (I) as defined previously, characterized in that acetylserine is made to react with an enzyme with an 'evolved cysteine synthase' activity as defined previously, in an appropriate reaction medium containing a sulfur compound of general formula (II) defined previously.

The appropriate reaction medium is a usual enzyme reaction medium, well known to those skilled in the art, in particular an aqueous medium in which the substrates and the enzyme are dissolved or suspended. The operating conditions for the reaction are well known to those skilled in the art, in particular those required to prevent substantial denaturing of the enzyme.

In a particular embodiment of the invention, the enzyme with an 'evolved cysteine synthase' activity is present in an inactivated bacterium or in a cell extract.

D.III. The Evolution of NADPH-Dependent Pathways

In another preferred embodiment of the invention, a NADPH-dependent pathway can be caused to evolve. To this end the initial bacterial strain must be modified in such a way that the rate of production of NADPH is greater than its rate of oxidation to NADP+ (also designated NADP), which will prevent growth of the bacteria on the defined medium selected to implement the method.

This invention concerns strains of microorganisms modified to permit the evolution of metabolic pathways that consume NADPH. The strains according to the invention can be used in biotransformation processes that consume NADPH.

This invention further concerns a method for the preparation of chemical entities by biotransformation involving the growth in an appropriate medium of a strain according to the invention, which strain also possesses the genetic features necessary for the preparation of such chemical entities.

Biotransformation processes have been developed to permit the production of large quantities of chemical entities at low cost, while at the same time putting to good use various industrial or agricultural by-products.

There are two main approaches to producing chemical entities of interest by in vivo biotransformation:

first, fermentation, which allows the production of chemical entities from a simple carbon source (e.g., WO0102547, which describes the production of lysine by fermentation of *C. glutamicum* in the presence of glucose), second, bioconversion by a microorganism of a given substrate different from the simple carbon source, which is used solely to produce the necessary biomass, for the production of a chemical entity of interest (e.g., WO0012745, which describes the production of R-piperidine derivatives, and WO0068397, which describes the production of Tagatose).

The improvement of a biotransformation process can involve various factors such as temperature, oxygenation, the composition of the medium, the recovery process, etc. It is also possible to modify the microorganism in such a way that the production and/or excretion of the chemical entity of interest is increased.

For fermentation, efforts may be directed, for example, to optimizing the biosynthesis pathway by, for example, modifying the regulation of genes or by modifying genes to modify enzyme characteristics or by optimizing the regeneration of co-substrates.

For bioconversion, efforts may be directed to improving the kinetic characteristics of enzymes, to reducing the formation of co-products and to optimizing the regeneration of co-substrates involved in the bioconversion step or steps.

Among the co-substrates involved in biotransformations, NADPH is important, in particular for the production of amino acids (e.g., arginine, proline, isoleucine, methionine or lysine), vitamins (e.g., pantothenate, phylloquinone or tocopherol), aromatic compounds (e.g., WO9401564), or other chemicals with high added value.

This invention concerns strains of microorganisms modified to cause the evolution of enzymes or metabolic pathways that consume NADPH.

For the creation of such microorganisms, the inventors chose modifications that increase the rate of production of NADPH and reduce its rate of oxidation to NADP+, which modified microorganisms are then used to cause the evolution of enzymes or metabolic pathways that consume NADPH. These bacteria can also be used judiciously in biotransformation processes for the production of chemical entities derived from NADPH-dependent synthesis pathways.

The optimization of NADPH is described below for E. coli. The same principle can be applied in a similar way to all microorganisms grown in aerobic conditions.

The strains modified according to the invention have undergone the deletion of the gene udhA and/or the gene qor. In a preferred embodiment of the invention, the genes udhA and qor are both deleted.

In a particular embodiment of the invention the strain modified according to the invention has also undergone the deletion of a gene selected from among pgi or pfkA and or pfkB.

The above genes are well known to those skilled in the art and are described in the scientific literature, in particular for E. coli:

Genes and References in E. coli:
udhA: X66026 soluble pyridine transhydrogenase;
qor: L02312 quinone oxidoreductase;
pgi: X15196 phosphoglucose isomerase (EC 5.3.1.9);
pfkA: X02519 phosphofructokinase-1;
pfkB: K02500 phosphofructokinase-2.

A further object of this invention is an evolved microorganism modified for the production of NADPH as described above and below, which also possesses one or more genes coding for NADPH-dependent enzymes involved in the biotransformation of a chemical entity of interest, which enzymes it is intended to cause to evolve, together with one or more selection marker genes.

These genes can be native to the modified strain according to the invention or be introduced into the optimized strain according to the invention by transformation with an appropriate vector, either by integration in the genome of the microorganism, or by a replicative vector, which vector possesses one or more genes coding for the enzymes involved in the bioconversion of the said chemical entity of interest or the said selection markers.

These genes contain a nucleic acid sequence coding for an enzyme involved in the biotransformation of the chemical entity of interest and/or for a selection marker, the coding sequence being attached to efficient promoter sequences in the prokaryotic and/or eukaryotic cell selected for the biotransformation. The vector (or plasmid) can be a shuttle vector between E. coli and another microorganism.

This invention further concerns a method for the preparation of modified strains according to the invention as defined above and below, in which the genes udhA and/or qor, and if necessary the genes pgi or pfrA and/or pfkB are deleted.

In a particular embodiment of the invention the method of preparation of the strains also includes the transformation of the modified strains with at least one appropriate vector with one or more genes coding for one or more NADPH-consuming enzymes involved in the biotransformation of a chemical entity of interest, and one or more selection marker genes. The vector allows either the replication of the genes or their integration in the chromosome of the modified bacterium. The transformation of the strain by the vector defined above can be carried out on the modified strain or before the modification of the strain according to the invention.

The strain modified for the production of NADPH is obtained by molecular biology methods.

A further aspect of the invention concerns the use of these modified strains according to the invention to cause the evolution of NADPH-dependent enzymes to improve their kinetic characteristics, to broaden or to narrow their substrate specificity, and ultimately to create a new metabolic pathway and/or to improve biotransformation yields. A further aspect of the invention concerns the use of the modified strain or the evolved strain to carry out biotransformation reactions that consume NADPH with biotransformation yields greater than those obtained with an unmodified and/or non-evolved strain.

The invention further concerns a method for the production of a chemical entity of interest synthesized by a NADPH-consuming process, characterized in that it comprises the following steps:

a) Culture of evolved microorganisms according to the invention in an appropriate culture medium that favors their growth and that contains the substances necessary to carry out the biotransformation by fermentation or bioconversion, except for NADPH.

b) Extraction of the chemical entity of interest from the medium and, if necessary, its purification.

The chemical entity of interest is preferably selected from among cysteine, methionine, 3-hydroxypropionate, hydrocortisone, xylitol and glycerol.

For a bioconversion reaction the method also includes the addition to the appropriate culture medium of the substrate to be converted.

The culture medium of step b) of the method according to the invention defined above contains at least one assimilatable carbohydrate chosen from among the different assimilatable sugars such as glucose, galactose, sucrose, lactose, or molasses, or by-products of these sugars. An especially preferred simple carbon source is glucose. Another preferred simple carbon source is sucrose. The culture medium can also contain one or more substances (e.g., amino acids, vitamins, mineral salts, etc.) that favor the production of the chemical entity of interest.

The examples given below illustrate the invention but do not restrict its scope.

E. DESCRIPTION OF FIGURES

FIG. 1: Synthesis of methionine from homoserine in bacteria.

Figure 2:
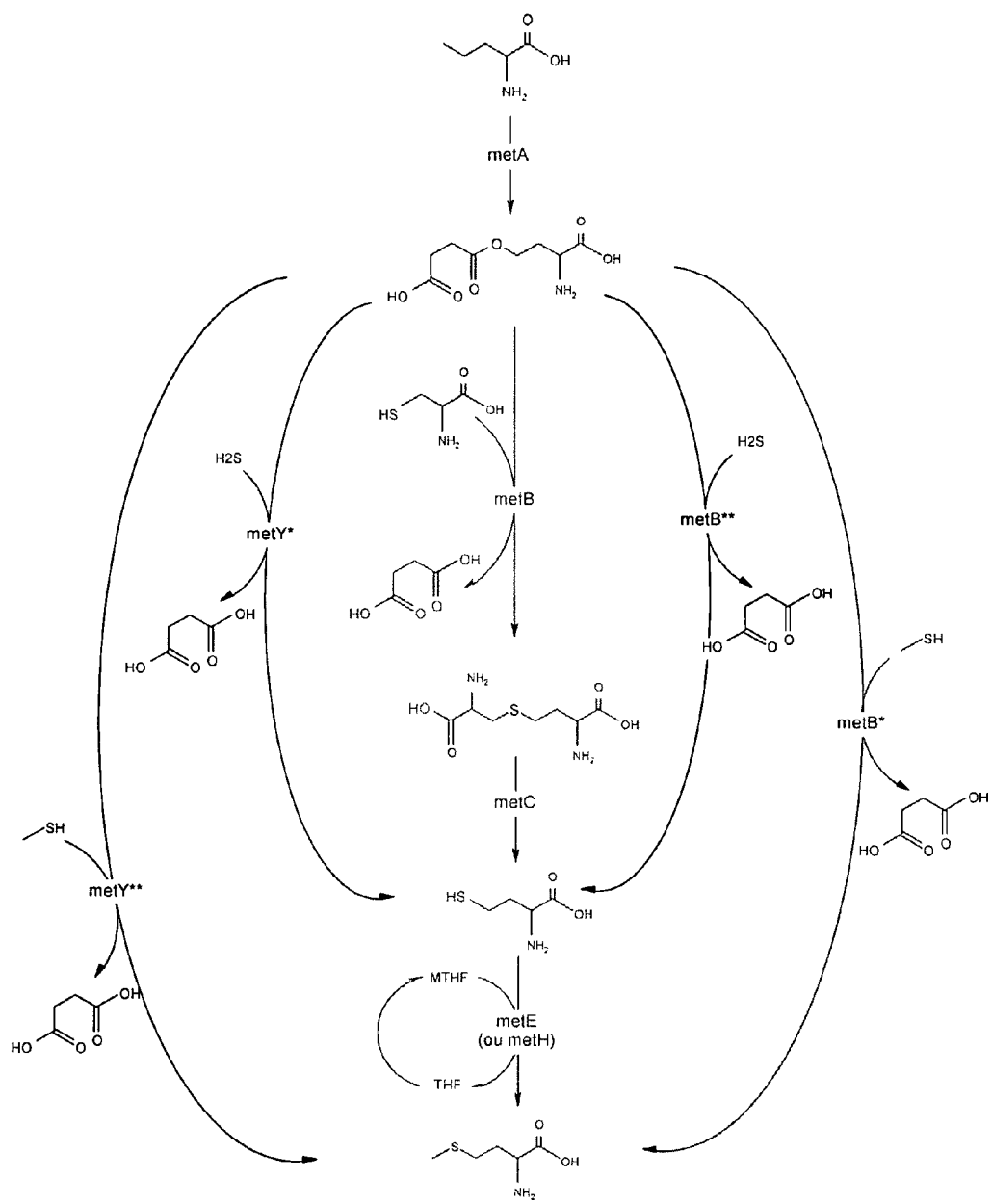

FIG. 2: Scheme for the synthesis of methionine according to the invention applied in *E. coli*; an equivalent strategy is transposable to many microorganisms including *C. glutamicum*. The metB* or metY strategies require the use of a strain that is initially at least Δ(metE), while the metB or metY* strategies require the use of a strain that is initially at least Δ(metC).

Legend

MetA: homoserine succinyltransferase; can be replaced by an isoform that is insensitive to feedback inhibition by methionine, or possibly by a homoserine acetyltransferase isoform that is insensitive to feedback inhibition by methionine.

MetB: cystathionine γ-synthase

MetB*: cystathionine γ-synthase evolved into 'methionine synthase'

MetB**: cystathionine γ-synthase evolved into homocysteine synthase

MetY*: O-acetyl-homoserine (de *C. glutamicum*) evolved into homocysteine synthase MetY**: O-acetyl-homoserine (de *C. glutamicum*) evolved into 'methionine synthase'

The central pathway represents the natural synthetic pathway of methionine in *E. coli*. The other pathways indicated correspond to the methods according to the invention.

Figure 3:
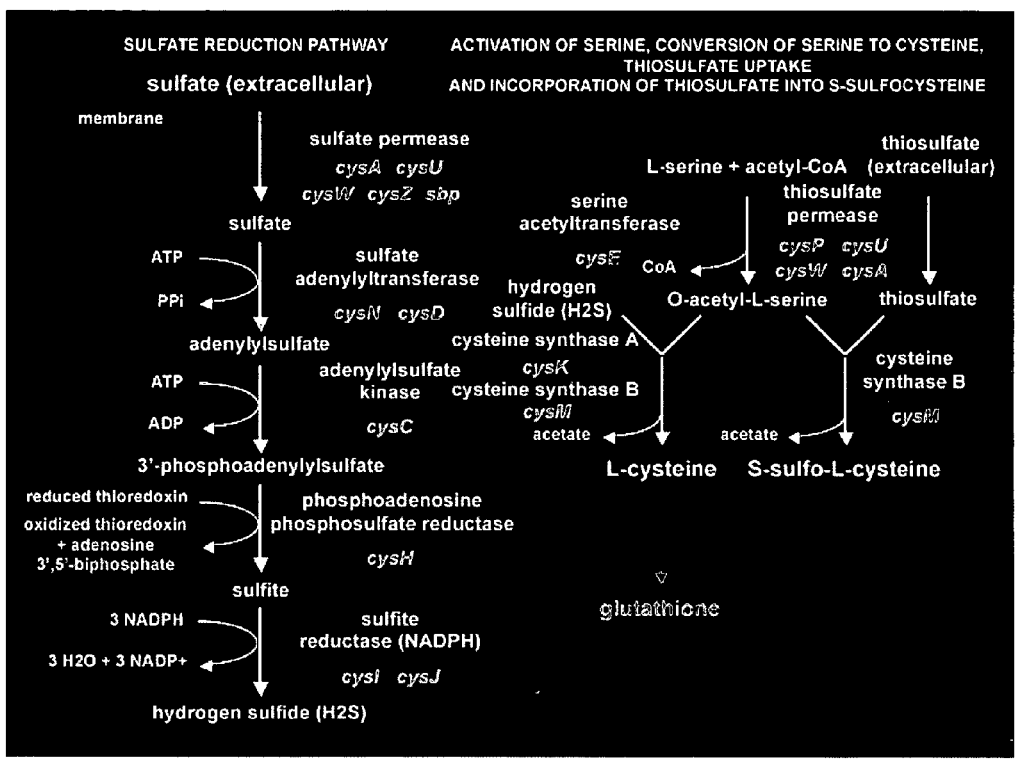

FIG. 3: Synthesis of cysteine from serine in bacteria.

FIG. 4: Strategy to achieve the synthesis of cysteine from O-acetyl-L-serine. The red arrow corresponds to the cysteine synthase activity of the enzyme coded for by the evolved gene metY according to the invention (metY*).

Figure 5:
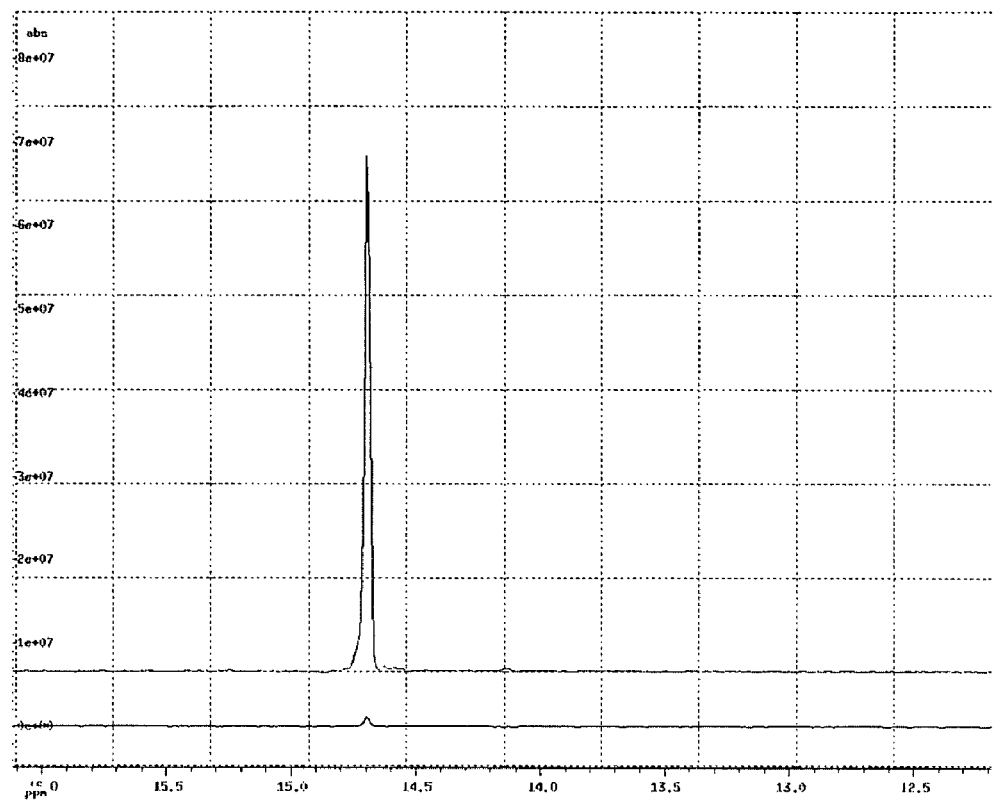

FIG. 5: Comparison of $^{13}$C-NMR spectra, corresponding to the 5-carbon of methionine, obtained by HSQC on a hydrolysate of the wild strain (top) or the optimized K1a-F strain (bottom). It can be observed that the 5-carbon of the strain K1a-F is not labeled by carbon 13, confirming that it originates from sodium methylmercaptide.

Figure 6:
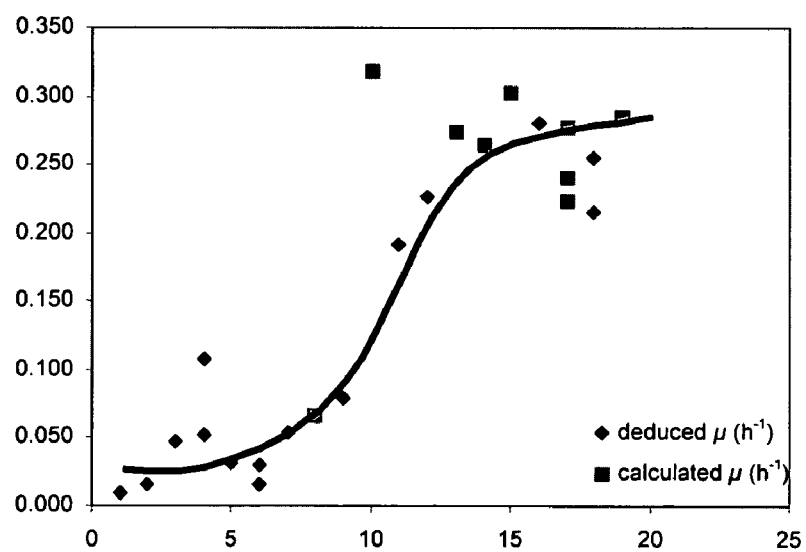

FIG. 6: Time course of the growth rate of the initial strain of *E. coli* Δ(metE) during the batchwise selection process. Abscissa: reseeding No.; Arrow: Population K144; deduced μ: values obtained from 2-3 values of OD; calculated μ: values obtained with more than 4 values of OD.

Figure 7:
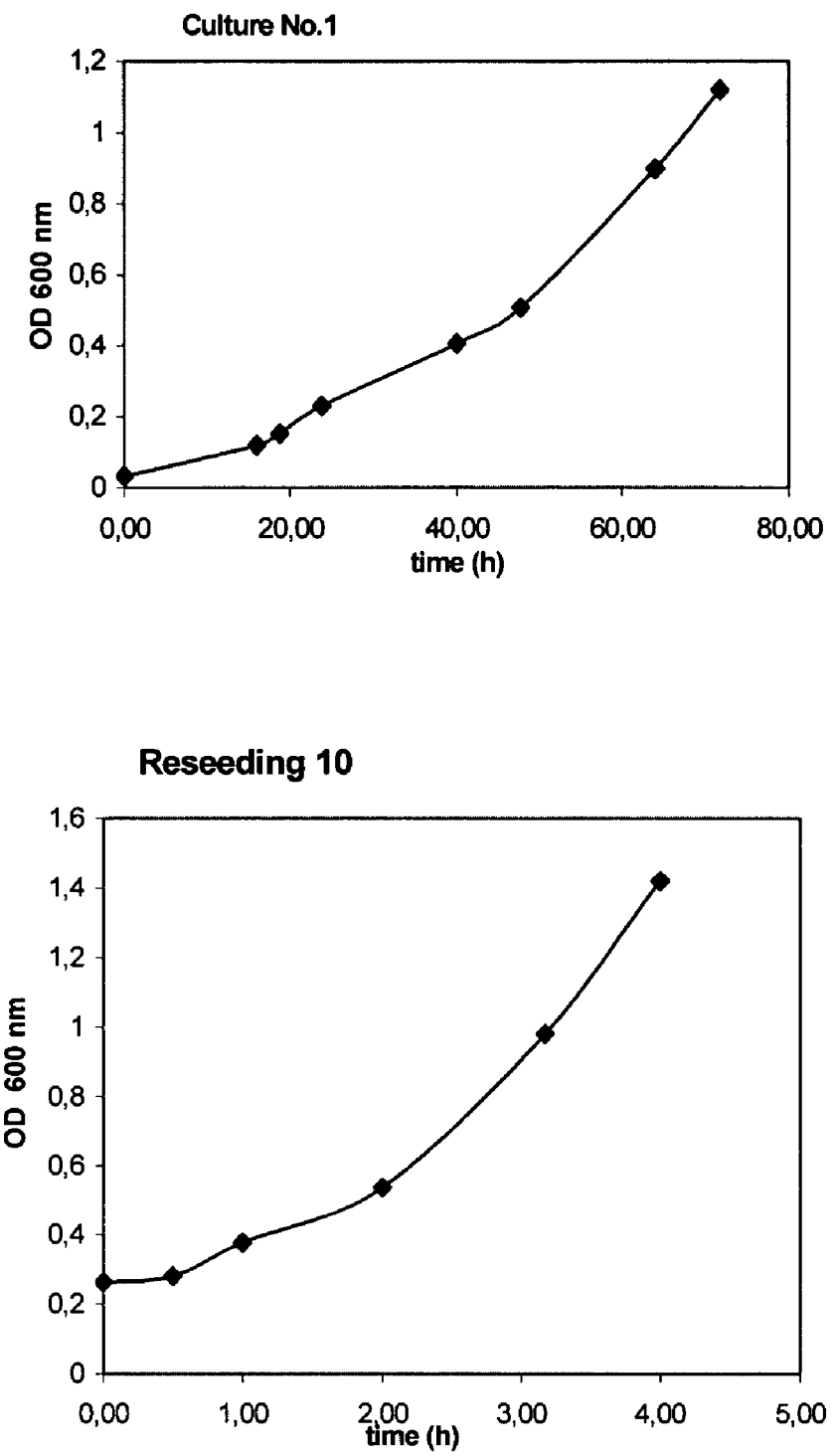

FIG. 7: Growth kinetics of the population of *E. coli* Δ(metC) after initial seeding (Culture 1) and after tenth reseeding (Reseeding 10).

Figure 8:
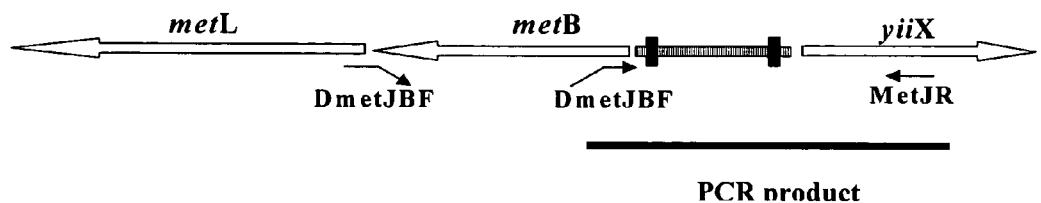

FIG. 8: Execution of PCR on the modified strain of *E. coli* ΔmetJ::Cm using starters DmetJBF and MetJR. The 5' end of the starter DmetJBF is also able to hybridise a sequence located in the 3' part of the gene metL.

Figure 9:
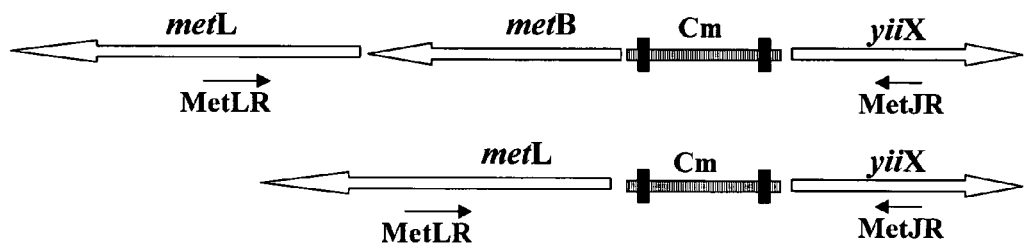

FIG. 9: Strains obtained after homologous recombination with the PCR-amplified fragment (see FIG. 8); it is possible to have two different homologous recombination events, each occurring with the same probability. In the first case, a strain *E. coli* ΔmetJ::Cm is recreated, while in the second case the strain *E. coli*[ΔmetJ, ΔmetJ::Cm] is created by replacement of the promoter of the operon metBLF before metL.

Figure 10:
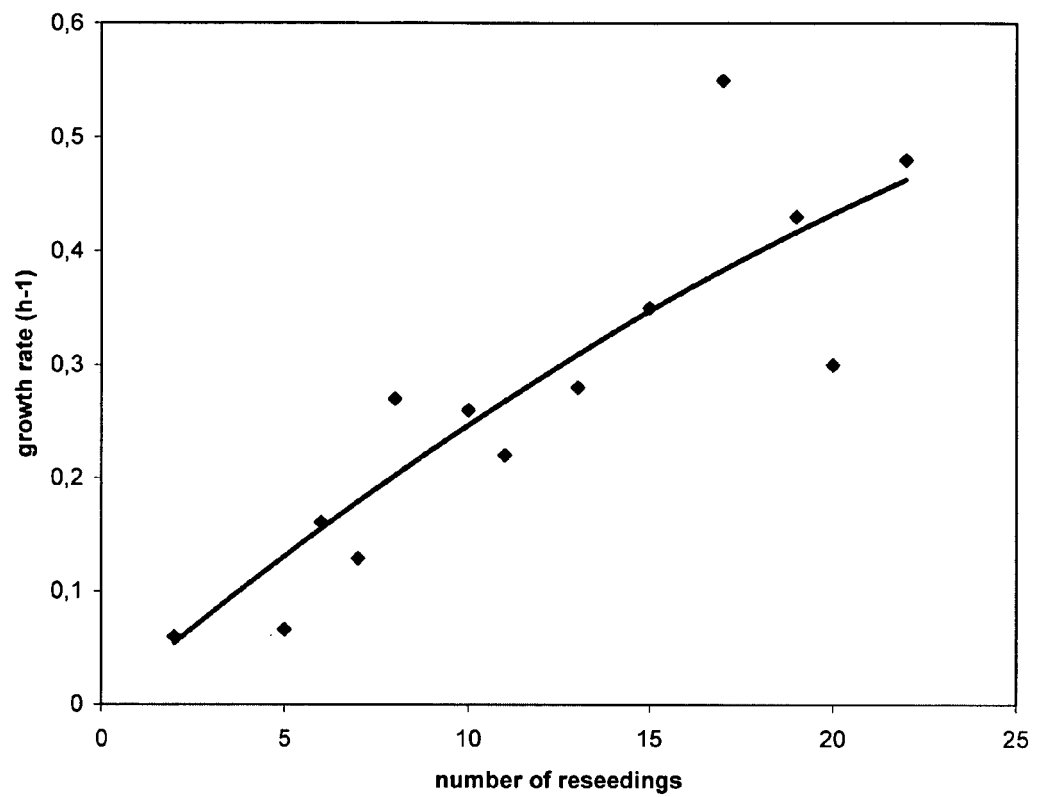

FIG. 10: Time course of the growth rate of the strain *E. coli* [Δ(metBJ, metC) pTrc-metY] on a defined medium (MML8) containing glucose as sole carbon source.

F. EXAMPLES

F.I. The Methionine Biosynthesis Pathway

A first application (Example F.I.1.) of the invention to the metabolic engineering of the biosynthesis pathway of methionine comprises the following steps:

a) Deletion of the gene metE in the initial strain of *E. coli*; the modified strain obtained is therefore auxotrophic for methionine. The initial strain is able to grow on a minimal medium (MM) containing no methionine, S-adenosylmethionine, homocysteine or cystathionine, whereas the modified strain has lost that ability.

b) Culture of the above modified strain on the same minimal medium (MM) to which sodium methylmercaptide (co-substrate) has been added to cause the evolution of an endogenous enzyme activity into a methionine-synthase activity to compensate for the initially deleted enzyme activity (MetE).

c) Selection of an evolved strain with a new methionine-synthase activity in the presence of sodium methylmercaptide, the strain being characterized.

d) Isolation of the evolved gene coding for the protein possessing an evolved enzyme activity, in this case cystathionine-γ-synthase with an improved methionine-synthase activity.

A second application (Example F.I.2.) of the invention to the metabolic engineering of the biosynthesis pathway of methionine comprises the following steps:

a) Deletion of the gene metC in the initial strain of *E. coli*; the modified strain obtained is thus auxotrophic for methionine. The initial strain is able to grow on a minimal medium (MM) containing no methionine, S-adenosylmethionine, homocysteine or cystathionine, whereas the modified strain has lost that ability.

b) Culture of the above modified strain on the same minimal medium (MM) in the absence of any co-substrate in order to cause the evolution of an endogenous enzyme activity into a homocysteine-synthase activity to compensate for the initially deleted enzyme activity (MetC).

A third application (Example F.I.3.) of the invention to the evolution of the biosynthesis pathway of methionine comprises the following steps:

a) Deletion of the genes metC, metB, and metJ in the initial strain of *E. coli*; the modified strain obtained is thus auxotrophic for methionine. The initial strain is able to grow on a minimal medium (MM) containing no methionine, S-adenosylmethionine, homocysteine or cystathionine, whereas the modified strain has lost that ability.

a1) Introduction of the gene metY, a heterologous gene from *C. glutamicum*. This gene is to evolve from an acetylhomoserine sulfhydrylase activity into a methionine-synthase activity.

b) Culture of the modified strain *E. coli* [metY Δ(metB, metC, metJ)] on the same minimal medium (MM) to which is added sodium methylmercaptide (co-substrate) to cause the evolution of an endogenous enzyme activity into a methionine-synthase activity to compensate for the initially deleted enzyme activities (MetB, MetC).

c) Selection of an evolved strain possessing a new methionine-synthase activity in the presence of sodium methylmercaptide.

Example F.I.1

Preparation of an Evolved Strain Possessing a Methionine-Synthase Activity in the Presence of Sodium Methylmercaptide a) Construction of the Modified Strain E. coli Δ(metE)

The inactivation of the gene metE is achieved by inserting a chloramphenicol resistance gene cassette and at the same time deleting most of the gene concerned. The method used is described by Datsenko, K. A., Wanner, B. L. (2000) One-step inactivation of chromosomal genes in Escherichia coli K-12 using PCR products. Proc. Natl. Acad Sci. USA 97: 6640-6645.

Two oligonucleotides were used to implement this strategy:
DmetER with 100 bases (SEQ ID NO 1):

```
tacccccgacgcaagttctgcgccgcctgcaccatgttcgccagtgccgcgcgggtttctggccagccgcgcgttt tcagCATATGAATATCCTCCTTAG
``` with:
- a region (lower case) homologous to the sequence (4012903 to 4012824) of the gene metE
- a region (upper case) for the amplification of the chloramphenicol resistance cassette of the plasmid pKD3 (Datsenko, K. A., Wanner, B. L. (2000) One-step inactivation of chromosomal genes in Escherichia coli K-12 using PCR products. Proc. Natl. Acad. Sci. USA 97: 6640-6645).

DmetEF de 100 bases (SEQ ID NO 2):

```
tgacaatattgaatcacaccctcggtttccctcgcgttggcctgcgtcgcgagctgaaaaaagcgcaagaaagtta ttggTGTAGGCTGGAGCTGCTTCG
``` with:
- a region (lower case) homologous to the sequence (4010644 to 4010723) of the gene metE;
- a region (upper case) for the amplification of the chloramphenicol resistance cassette carried by the plasmid pKD3.

The oligonucleotides DmetER and DmetEF are used to amplify the chloramphenicol resistance cassette from the plasmid pKD3. The PCR product obtained is then introduced by electroporation into the strain MG1655 (pKD46) in which the enzyme Red recombinase expressed permits the homologous recombination. The chloramphenicol-resistant transformants are then selected and the insertion of the resistance cassette is verified by PCR analysis with the oligonucleotides metER and metEF.

MetER (SEQ ID NO 3): ggtttaagcagtatggtgggaagaagtcgc (homologous to the sequence from 4012978 to 4012949).

MetEF (SEQ ID NO 4): cccggggatgaataaacttgccgccttccc (homologous to the sequence from 4010567 to 4010596).

The chloramphenicol resistance cassette can then be eliminated. The plasmid pCP20 carrying the FLP recombinase acting at the FRT sites of the chloramphenicol resistance cassette, is then introduced into the recombinant strains by electroporation. After a series of cultures at 42° C., the loss of the chloramphenicol resistance cassette is verified by a PCR analysis with the same oligonucleotides as used previously.

b) Culture and Evolution of the Δ(metE) Modified Strain in the Presence of Sodium Methylmercaptide as Co-Substrate To optimize E. coli for the production of methionine from methylmercaptan, a controlled selection is carried out in flasks.

The E. coli strain made auxotrophic for methionine by inactivating the metE gene (see above) cannot grow unless it can make its own methionine from methylmercaptan.

The implementation of this method permits the selection of a strain of Escherichia coli of which the cystathionine-γ-synthase (EC 4.2.99.9) has acquired a modified 'methionine-synthase' activity in the presence of methylmercaptan.

The controlled selection is conducted in a hermetically sealed glass flask containing 50 ml of inorganic medium (Schaefer et al., 1999, Anal. Biochem. 270: 88-96) in the presence of 33 mM glucose and chloramphenicol at a final concentration of 25 mg/l.

The culture media are seeded with the strain E. coli K12 ΔmetE at a defined value of $OD_{600\,nm}$. Seeding is carried out with a sufficiently large population of bacteria so that some bacteria potentially possess relevant spontaneous mutations in the gene metB enabling assimilation of methylmercaptan. This population is obtained by culture of the strain auxotrophic for methionine on a minimal medium supplemented with methionine.

Three flasks then receive 100 μl of a 400 mg/l solution of sodium mercaptide, while a fourth flask has no added sodium mercaptide. The cultures are grown with shaking at 37° C., for 6 days, after which time the $OD_{600\,nm}$ is measured. The results are summarized in Table 1 below.

TABLE 1

Measurement of the optical density (OD) of culture media for E. coli in the presence (flasks 1-3) or absence (control flask) of sodium mercaptide.

|  | Flask 1 | Flask 2 | Flask 3 | Control flask |
|---|---|---|---|---|
| $OD_{600\,nm}$ at T = 0 | 0.34 | 0.34 | 0.34 | 0.34 |
| $OD_{600\,nm}$ at T = 6 days | 0.23 | 1.14 | 0.79 | 0.32 |

These results show that in flasks 2 and 3 a strain grows that is able to use methylmercaptan to produce the methionine necessary for its growth (increase in optical density).

c) Selection of the Evolved Strain in the Presence of Sodium Methylmercaptide

The population of E. coli Δ(metE) from flask 2, after undergoing successive reseedings in flasks, yields the population K1a-F.

The new population obtained K1a-F is cultured in a minimal medium (Schaefer et al., 1999, *Anal. Biochem.* 270: 88-96) containing 2.5 g.l$^{-1}$ of uniformly carbon 13-labeled glucose, and sodium methylmercaptide (200 ppm) with no carbon 13 enrichment. This population is auxotrophic for methionine in the absence of sodium methylmercaptide.

After culture, the cells are recovered, washed and hydrolysed with 6N HCl for 24 hours at 107° C. An analysis by 2D NMR is then carried out (HSQC). This analysis shows whether the 5-carbon of methionine comes from L-cysteine produced from the glucose present in the solution (classical pathway), or from the sodium methylmercaptide when the new metabolic pathway according to the invention is used.

The experiment is conducted in a similar manner with the wild strain *E. coli* K12 (producing methionine from glucose), in the absence of sodium methylmercaptide.

FIG. 5 shows two 1D spectra, derived from two separate acquisitions, superimposed for greater clarity. These 1D spectra were extracted from 2D NMR spectra of the HSQC type (correlation between protons and carbon 13). The 2D NMR spectra are obtained on an acid hydrolysate of the bacteria.

The sample analyzed is a total hydrolysate. However, given the sensitivity of the NMR and the acquisition times used, essentially amino acids, sugars, bases and glycerol are detected, each carbon atom (coupled to a proton) of each acid giving an NMR signal.

The 5-carbon of methionine (i.e., the terminal methyl group) presents a chemical shift of about 14.7 ppm. FIG. 5 shows the area of the chemical shift centered at 14.7 ppm for the two strains.

It can be seen that the signal of the 5-carbon is strong in the upper spectrum, indicating that the 5-carbon is labeled with carbon 13. Hence this 5-carbon comes from the labeled glucose introduced as a substrate in the culture medium.

In contrast, the same signal is very weak in the lower spectrum (strain K1a-F). This indicates that the 5-carbon is practically unlabeled. Yet the other carbons in the molecule are strongly labeled (results not presented). The unlabeled 5-carbon therefore comes not from glucose, but from methylmercaptan.

In can therefore be concluded that the strain K1a-F produces methionine from succinyl-L-homoserine and sodium methylmercaptide.

The population K1a-F undergoes 14 further successive reseeding cycles in flasks. In this way the population K144 is obtained (FIG. 6), which is then spread on gelosed minimal medium containing glucose as sole carbon source. The inoculated dishes are placed in aerobic conditions in an aerobic jar into which is inserted a tube containing sodium methylmercaptide dissolved in water. The jar is then placed in an incubator at 37° C. As the boiling point of methylmercaptan is 5° C., the atmosphere in the jar becomes enriched in methylmercaptan. After 4 days, clones appear in the dishes; these are bacteria able to produce methionine in the presence of methylmercaptan. Ten clones are isolated, including the clone K176. The clone K176 is grown in liquid culture and glycerol stocks are prepared, numbered K183.

For the clone K183 and the initial strain *E. coli* K12 Δ(metE), the sequence of the genes metJ and metB (SEQ ID No.5) is determined. The sequence obtained for evolved metB, designated metB* (SEQ ID No.7) reveals the presence of an alanine unit at position 325 (SEQ ID No.8) in place of a glutamate (SEQ ID No.6). The gene metJ shows no mutation. This strain is registered at the CNCM on Apr. 2 2003, under the number I-3005.

Characterization of the Clone K183

The clone K183 is grown in flasks in a minimal medium with glucose and sodium methylmercaptide as sole carbon source. In parallel, a culture is carried out under identical conditions with wild strain *E. coli* K12. The consumption of glucose per unit of biomass is found to be twice that of a wild strain of *E. coli* (MBM01). This over-consumption is probably partly due to acetate production.

TABLE 2

Comparison of biomass yield of wild strain *E. coli* and evolved clone K183:

| Strain | Biomass yield | Acetate yield |
|--------|---------------|---------------|
| MBM01  | 0.45          | <0.002        |
| K183   | 0.24          | 0.36          |

Biomass yield expressed as mass of biomass/mass of glucose

Acetate yield expressed as mass of acetate/mass of glucose

The analysis of intracellular and extracellular metabolites of these two cultures shows, in particular:

Intracellularly, an increase in alanine, pyruvate, ketobutyrate and 2-ketoisocaproate, and a decrease in the concentration of tryptophan, norvaline, norleucine, leucine andmethionine.

Extracellularly, an accumulation of glutamate, isoleucine, threonine, valine and 2-ketoisocaproate, and a decrease in pyruvate, norleucine, and tryptophan.

Characterization of the Specific 'Methionine Synthase' Activity of the Strains MBM01 and K183 in the Presence of Methylmercaptan.

To show the improvement of the methionine-synthase activity in the strain K183 relative to the wild strain (MBM01), enzyme reactions are carried out using cell-free extracts prepared from cultures of the strains K183 and MBM01 carried out on rich medium (BH1, marketed by DIFCO, with 2.5 g/L of glucose) in the absence of methylmercaptan. The protein extracts are desalted on PD10 and stored on ice.

Reaction Conditions and Sample Treatment

A solution of sodium methanethiolate diluted 10-fold (100 µl of 3M solution plus 900 µl of MilliQ water) is prepared on ice.

Reaction mixtures of 20 µL of 500 mM pH 6.5 phosphate buffer, 10µL of 2.5 mM pyridoxal phosphate, 16 µL of 25 mM O-succinylhomoserine, 10 µL of 0.3 M sodium methanethiolate, and 24 µL of MilliQ water are prepared on ice.

The tubes are placed at 37° C. (thermomixer under a hood) and the protein extract (20µl) added to start the reaction.

To quench the reaction (0 to 30 minutes), the tubes are placed on ice and 400 µl of acetone added at −20° C.

The tubes are left at −20° C. for 30 minutes.

The tubes are opened under the hood for 10 minutes to evaporate off methanethiol and acetone (kept on ice).

The mixture is centrifuged for 5 minutes at 10,000 g, the supernatant (~100 µl) decanted off into Eppendorf tubes and diluted to a final volume of 1 ml.

Measurement of the Methionine Synthase Activity by Detection of the Quantity of Succinate Released from Succinylhomoserine A 10 µl aliquot of the above sample is analyzed by ion chromatography using a Dionex DX-500 apparatus fitted with a 2 mm AG-11 precolumn and a 2 mm AS-11 column, an ASRS Ultra suppressor, and a 10 µl injection loop. A gradient is then applied: 0-7 min 0.5 mM KOH; 7 min injection; 7-9.5 min 0.5 mM KOH; 9.5-13 min 0.5-5 mM KOH; 13-25 min 5-38.3 mM KOH.

Measurement of the Methionine Synthase Activity by Detection of the Quantity of Methionine Synthesized in the Presence of Methylmercaptan The analysis is carried out by GC-MS, which requires the silylation of samples before injection. For this purpose each sample receives an internal standard (serine 13C) to allow the quality of the silylation to be validated. The samples are then lyophilized overnight.

The derivatization is carried out using the following protocol:

Using a 1 ml automatic pipette 400 µl of hydroxylamine solution (0.250 g ±0.002 g dissolved in 10 ml of pyridine) is added, making sure the tubes were tightly closed. The mixture is vortexed twice for 10 seconds, centrifuged to concentrate it at the bottom of the tube (max. 1 minute at 5000 g) and left to react for 1½ hours at 30° C. The tubes are opened and 1000 µl of BSTFA solution is added using a 1 ml automatic pipette, topping up with 100 µl of pyridine (200 µl automatic pipette). The tubes are closed, vortexed for 10 seconds and left to incubate respectively for 60 minutes at 60° C. for TBDMS derivatives and 30 minutes at 70° C. for BSTFA. If necessary the samples are filtered on a disposable filter with a 0.22 µm PTFE membrane or centrifuged at 5000 g for 5 minutes. They are transferred to 1.5 ml flasks, sealed and injected into the GPC.

The analyses are carried out with an Agilent Technologies GC6890/MSD5973 apparatus fitted with a non-polar column (HP-5MS, Bios Analytique). The carrier gas is helium with a constant flow rate of 1 ml.min$^{-1}$. The injection of 1 µl of sample is in splitless mode with a purge flow rate of 50 ml.min$^{-1}$ for 0.85 min. The temperature profile is: initial temperature 90° C. maintained for 2 minutes and then increased to 320° C. with a gradient of 10° C. min$^{-1}$. This temperature is maintained for 6 minutes. Detection is by mass spectrometry with ionization by electron impact in scanning mode in the range m/z=40 to 550 amu. The solvent passage time is set at 3.10 minutes.

Under these conditions, a 'methionine synthase' activity can be assayed in the samples incubated with methanethiol, by the quantification first of succinate by ion chromatography and second of methionine by GC-MS.

The results are given in Table 3 below.

TABLE 3

Methionine synthase activity in the presence of methylmercaptan of extracts from strains MBM01 and K183

| Strain | Protein concentration | Specific activity (mUI/mg protein) | |
|---|---|---|---|
| | | Succinate assay | Methionine assay |
| MBM01 | 3.43 | 0.30 | 0.23 |
| K183 | 3.62 | 1.40 | 1.72 |

It is thus evident that the methionine synthase activity in the presence of methylmercaptan is strengthened in the evolved strain relative to the wild strain, confirming that the mutated cystathionine γ-synthase (E325A) has a modified methionine synthase activity.

d) Isolation of the Evolved Gene and Kinetic Characterization of the Enzyme METB* Possessing an Evolved Methionine-Synthase Activity To determine the kinetic parameters of the methionine-synthase and cystathionine-γ-synthase activities exerted by METB and METB*, the genes metB and metB* are cloned in an overexpression vector pTopo (Invitrogene) using the following strategy:

Amplification of the gene metB or metB* with the oligonucleotides metJ/metLR and heat-resistant polymerase Pwo.

Ligation of the PCR product to the plasmid pTOPO 4-PCR blunt, and introduction of the plasmid thus formed, pTopo.metB or pTopo.metB* into DH5α and selection of Ap$^r$ clones.

Verification by enzymatic digestion of the configuration of the plasmid pTopo.metB ou pTopo.metB* after extraction.

Introduction of the verified plasmid pTopo.metB into the strain MG1655(ΔmetBJ, ΔmetE). Verification by enzymatic digestion, as previously described, of the introduced plasmid. Verification by PCR of the strain MG1655(ΔmetBJ, ΔmetE) with the oligonucleotides metJR/metLR for the deletion metJ, and metER/metEF for the deletion metE: strain MINS33.

Cultures are then carried out on rich medium and protein extracts are prepared. The methionine-synthase and cystathionine-γ-synthase enzyme activities are then determined using sodium methylmercaptide and cysteine as reaction co-substrates, respectively. The kinetic characteristics of the methionine synthase activity are given in Table 4. The kinetic characteristics of the cystathionine-γ-synthase activity are given in Table 5.

TABLE 4

Apparent kinetic characteristics of the methionine-synthase activity of enzymes METB and METB*.

| | $K_m$ | $V_{max}$ |
|---|---|---|
| pTOPOmetB | 277 mM | 13.9 mUI/mg protein |
| PTOPOmetB* | 6 mM | 5.6 mUI/mg protein |

The effect of the mutation A325E is to reduce the $K_m$ of the enzyme 45-fold for methylmercaptan, whereas $V_{max}$ is only halved.

TABLE 5

Apparent kinetic characteristics of the cystathionine-γ-synthase activity of enzymes METB and METB*.

| | $K_m$ | $V_{max}$ |
|---|---|---|
| pTOPOmetB | 7.5 mM | 39840 mUI/mg protein |
| PTOPOmetB* | 0.6 mM | 2889 mUI/mg protein |

The effect of the mutation A325E reduces the cystathionine-γ-synthase activity 13-fold and the $K_m$ of the enzyme for cysteine.

Example F.I.2

Evolution of a Homocysteine Synthase Activity from a Cystathionine-γ-Synthase

Construction of Strains MG1655 (ΔmetC::Cm) and MG1655 (ΔmetC)

To inactivate the gene metC the homologous recombination strategy described by Datsenko & Wanner (2000) is used. This strategy permits the insertion of a chloramphenicol resistance cassette, while deleting most of the gene concerned. For this purpose 2 oligonucleotides are used:

For metC:

DmetCR with 100 bases (SEQ ID NO 13):

```
ccggcgtccagatcggcaatcagatcgtcgacatcttccagaccaatatgcaggcgaatcaaggtcccgctaaaat
cgatCATATGAATATCCTCCTTAG
``` with
- a region (lower case) homologous to the sequence (3151419 to 3151359) of the gene metC,
- a region (upper case) for the amplification of the chloramphenicol resistance cassette (reference sequence in Datsenko, K. A. & Wanner, B. L., 2000, PNAS, 97: 6640-6645), DmetCF with 100 bases (SEQ ID NO 14):

```
cggacaaaaagcttgatactcaactggtgaatgcaggacgcagcaaaaaatacactctcggcgcggtaaatagcgt
gattTGTAGGCTGGAGCTGCTTCG
``` with
- a region (lower case) homologous to the sequence (3150255 to 3150334) of the gene metC
- a region (upper case) for the amplification of the chloramphenicol resistance cassette.

The oligonucleotides DmetCR and DmetCF are used to amplify the chloramphenicol resistance cassette from the plasmid pKD3. The PCR product obtained is then introduced by electroporation into the strain MG1655 (pKD46) in which the Red recombinase enzyme expressed permits the homologous recombination. The chloramphenicol resistant transformants are then selected and the insertion of the resistance cassette is verified by a PCR analysis with the oligonucleotides metCR and metCF defined previously. The strain retained is designated MG1655 (ΔmetC::Cm).

MetCR (SEQ ID NO 11): cgtccgggacgccttgatcccggacgcaac (homologous to the sequence from 3151522 to 3151493).

MetCF (SEQ ID NO 12): gcgtttacgcagtaaaaaagtcaccagcacgc (homologous to the sequence from 3150118 to 3150149).

The chloramphenicol resistance cassette can then be eliminated. The plasmid pCP20 carrying recombinase FLP acting at the FRT sites of the chloramphenicol resistance cassette is then introduced into the recombinant strains by electroporation. After a series of cultures at 42° C., the loss of the chloramphenicol resistance cassette is verified by a PCR analysis with the same oligonucleotides as those used previously. The strain retained is designated MG1655 (ΔmetC).

The construction of the strain Δ(metC) is described in Example F.I.2. In a particular embodiment of the invention the strain E. coli Δ(metC) is cultured in flasks (see Example F.I.1) containing a minimal medium with glucose as sole carbon source. The medium contained neither methylmercaptan nor $H_2S$. Reseeding is carried out and growth rates are determined for each reseeding. A very marked improvement in the growth rate of the strain Δ(metC) is observed on the minimal medium, suggesting that the homocysteine synthase activity of the cystathionine γ-synthase is strongly improved in the presence of endogenous $H_2S$ (see FIG. 7).

EXAMPLE F.I.3.

Evolution of a methionine synthase activity from an acetylhomoserine sulfhydrylase activity.

| Reseeding cycle number | measured μ (h$^{-1}$) |
|---|---|
| 1 | 0.05 |
| 3 | 0.37 |
| 5 | 0.39 |
| 10 | 0.44 |
| 12 | 0.44 |

Construction of the Strain MG1655 (ΔmetB-ΔmetJ)

To delete the genes metB and metJ, and conserve the promoter of the operon metBL, a chloramphenicol resistance cassette is inserted, while at the same time deleting most of the genes concerned and maintaining the promoter of metBL. For this purpose we use 2 oligonucleotides.

For metBJ:

MetJR with 30 bases (SEQ ID NO 9):

```
ggtacagaaaccagcaggctgaggatcagc
``` homologous to the sequence (4125431 to 4125460) downstream of the gene metJ.

DmetJBF with 100 bases (SEQ ID NO 10):

```
tatgcagctgacgacctttcgccctgcctgcgcaatcacactcattttaccccttgtttgcagcccggaagcca
ttttcaggcaccagagtaaacatt
``` with
a part (upper case) homologous to the sequence (4126217 to 4126197) between the genes metJ and metB (sequence 4126252 to 4127412) containing the promoter region of the operon metBLF,
a part (lower case) homologous to the sequence (4127460 to 4127380) corresponding to the beginning of the gene metL (sequence 4127415 to 4129847) and the end of the gene metB.

These two oligonucleotides were used to amplify the region concerned on the chromosomal DNA of MG1655 Δ(metJ::Cm); see FIG. 8.

The PCR product obtained is then introduced by electroporation into the strain MG1655 (pKD46) in which the Red recombinase enzyme expressed permits the homologous recombination. The chloramphenicol resistant transformants are then selected and the deletion of the gene metB by homologous recombination is verified by PCR analysis with the oligonucleotides MetJR and MetLR, defined previously.

The desired strain is strain MG1655 (ΔmetB-ΔmetJ::Cm) in which the genes metJ and metB are eliminated and the promoter of the operon metBLF repositioned before metL (see FIG. 9).

The chloramphenicol resistance cassette can then be eliminated. The plasmid pCP20 carrying FLP recombinase acting at the FRT sites of the chloramphenicol resistance cassette is then introduced into the recombinant strains by electroporation. After a series of cultures at 42° C., the loss of the chloramphenicol resistance cassette is verified by PCR analysis with the same oligonucleotides as used previously (MetLR and MetJR).

Construction of the Strains MG1655 Δ(metC::Cm, metJB) and MG1655 Δ(metC, metJB)

To delete the gene metC, the method of phage P1 transduction is used. The protocol followed is implemented in 2 steps with the preparation of the phage lysate on the strain MG1655 Δ(metC::Cm) and then transduction into strain MG1655 Δ(metB-ΔmetJ).

The construction of the strain Δ(metC::Cm) is described in Example F.I.2.

Preparation of Phase Lysate P1:
Seeding with 100 µl of an overnight culture of the strain MG1655 (ΔmetC::Cm) of 10 ml of LB+Cm 30 µg/ml+ glucose 0.2%+CaCl$_2$ 5 mM.
Incubation for 30 min at 37° C. with shaking.
Addition of 100 µl of phage lysate P1 prepared on the wild strain MG1655 (about 1.10$^9$ phage/ml)
Shaking at 37° C. for 3 hours until all the cells were lysed.
Addition of 200 µl of chloroform and vortexing.
Centrifuging for 10 min at 4500 g to eliminate cell debris.
Transfer of supernatant to a sterile tube and addition of 200 µl of chloroform.
Storage of lysate at 4° C.
Transduction
Centrifuging for 10 min at 1500 g of 5 ml of an overnight culture of the strain MG1655 (ΔmetB-ΔmetJ) in LB medium.
Suspension of the cell pellet in 2.5 ml of 10 mM MgSO$_4$, 5 mM CaCl$_2$
Control tubes: 100 µl cells
100 µl phages P1 of strain MG1655 (ΔmetC::Cm)
Test tube: 100 µl of cells+100 µl of phages P1 of the strain MG1655 (ΔmetC::Cm)
Incubation for 30 min at 30° C. without shaking.
Addition of 100 µl of 1 M sodium citrate in each tube and vortexing.
Addition of 1 ml of LB
Incubation for 1 hour at 37° C. with shaking
Spreading on dishes LB+Cm 30 µg/ml after centrifuging of tubes for 3 min at 7000 rpm.
Incubation at 37° C. overnight.

Verification of the Strain

The cloramphenicol transformants are then selected and the insertion of the region containing (metC::Cm) is verified by a PCR analysis with the oligonucleotides MetCR and MetCF, and MetJR and MetLR to verify also the strain with genes metB and metJ. The strain retained is designated MG1655 Δ(metC::Cm, metJB).

MetCR (SEQ ID NO 11): cgtccgggacgccttgatcccggacgcaac (homologous to sequence 3151522 à 3151493)

MetCF (SEQ ID NO 12): gcgtttacgcagtaaaaaagtcaccagcacgc (homologous to the sequence from 3150118 to 3150149).

As previously, the chloramphenicol resistance cassette can then be eliminated. The plasmid pCP20 carrying FLP recombinase acting at the FRT sites of the chloramphenicol resistance cassette is then introduced into the recombinant sites by electroporation. After a series of cultures at 42° C., the loss of the chloramphenicol resistance cassette is verified by a PCR analysis with the same oligonucleotides as used previously (MetCR and MetCF, and MetJR and Met LR). The strain retained is designated MG1655 Δ(metC, metJB).

Introduction of the Plasmid pTrc99A-metY and Evolution of the Strain

In a particular embodiment, a plasmid is constructed that permits the expression of the gene metY of *C. glutamicum*. This gene is amplified by PCR from chromosomal ADN of *C. glutamicum* and introduced into a plasmid pTrc99A. It is possible to amplify by PCR the gene metY and if necessary its natural promoter. In a preferred embodiment, the gene metY is cloned under the control of a promoter that permits an expression in *E. coli*. The vector used is a pTrC99A (Pharmacia), but a vector selected from among pUC, pBluescript, pCR-Script, pTopo, etc. could also be used.

The strain *Escherichia coli* Δ(metC, metJB) obtained previously is transformed with the plasmid pTrc-metY of *C. glutamicum*. The transformation of the strain is carried out by electroporation.

The strain obtained is then inoculated in a conical flask (OD$_{600\,nm}$ ~0.4-0.5) containing 10% of its volume in a minimal medium with glucose for sole carbon source. The low succinylhomoserine sulfhydrylase activity initially carried by the enzyme MetY limits the growth (µ~0.06 h$^{-1}$) of the bacterial population on the minimal medium (MML8) owing to limitation of synthesized methionine. Reseeding is carried out when the OD$_{600\,nm}$ in the flask reached about 2. The selection is thus conducted for 22 culture cycles. A marked improvement in the growth rate is observed during this phase of evolution-selection (FIG. 10). In view of prior experience, it is likely that the improvement in growth observed corresponds to an evolution of the gene metY such that the O-acetyl-homoserine sulfhydrylase activity is changed into an O-succinyl-homoserine sulfhydrylase activity allowing the production of homocysteine from O-succinylhomoserine and H$_2$S; these two substrates being produced by the bacterium.

To optimize the process of evolution of metY, a similar approach is possible using other mutants of *Escherichia coli*, in particular the mutant Δ(metC, metB).

Example F.I.4

Fed-Batch Culture Process for the Production and Purification of Methionine

Pre-Culture

The pre-culture is carried out overnight in a 500 ml flask containing 50 ml of minimal medium, type M9 modified, supplemented with 2.5 g/l of glucose. The cells are recovered by centrifuging and taken up in 5 ml of minimal medium, type M9 modified.

Culture in a Fermenter

The culture is carried out in a fermenter with a useable volume of 300 ml of the Fedbatch-pro DASGIP type.

The fermenter is filled with 145 ml of minimal medium, type M9 modified, and inoculated with 5 ml of pre-culture, i.e., an inoculation OD600 nm between 0.5 and 1.2.

The temperature of the culture is maintained between 30 and 37° C. and the pH is continuously adjusted to a value between 6.5 and 8. It is partially regulated by adding a solution of $CH_3SNa$. A solution of 2N sodium hydroxide can if necessary be used to complete the regulation. Shaking is maintained at between 200 and 400 rpm during the batch phase and is increased to 1000 rpm at the end of the fed-batch process. The dissolved $O_2$ content is maintained between 30% and 40% saturation using a gas controller. As soon as the $OD_{600\ nm}$ attains a value between 2.5 and 3 the fed-batch process is started by adding the fed medium at an initial flow rate of between 0.3 and 0.5 ml/h with a gradual increase to flow rates between 2.5 and 3.5 ml/h. Thereafter the flow rate is maintained constant for between 24 h and 32 h. The fed medium is made up on the basis of a modified M9 medium complemented by a glucose concentration between 300 and 500 g/l of glucose. At the same time the medium is supplemented with a solution of $CH_3SNa$ (solution between 1 and 5 M) to allow bacterial growth while at the same time regulating the pH. As soon as the cell concentration reaches a value between 20 and 50 g/l the fed medium is replaced by a minimal medium of type M9 with limited phosphorus. The solution of methylmercaptan is replaced by a direct injection of $CH_3SH$ in gaseous form into the fermenter. The gas flow rate is adapted to the flow rate of the fed solution in molar ratios to the carbon substrate ranging from 1 to 3. As soon as the cell concentration is between 50 and 80 g/l the fermentation is stopped. The pH of the fermentation must liquor is adjusted to between 7.5 and 9 with a solution of NaOH, and it is heated to between 60 and 80° C. The liquor is then filtered on UF modules. The temperature of the liquor is maintained at between 60 and 80° C., and the liquor is then concentrated before running it through charcoal to de-color it (in a column or batchwise). The de-colored liquor is filtered again to remove last particles before acidification with concentrated HCl to a pH below 2.28 ($pK_1$ of methionine). The crystals of methionine hydrochloride thus formed are recovered by filtration and the HCl eliminated by evaporation, yielding purified L-methionine.

Registration of Biological Material

The strain K183 was registered on Apr. 2 2003 at the Collection Nationale de Cultures de Microorganismes (CNCM), 25 rue du Docteur-Roux, 75724 Paris Cedex 15, France, in compliance with the provisions of the Treaty of Budapest, under the serial number I-3005.

F.II. Evolution of the Cysteine Biosynthesis Pathway

One application (Example F.II.1.) of the invention to metabolic engineering of the biosynthesis pathway of cysteine comprises the following steps:

a) Deletion of the genes cysK, cysM in the initial strain of *E. coli*; the modified strain obtained is thus auxotrophic to cysteine. The initial strain is able to grow on a minimal medium (MM) containing no methionine, S-adenosyl-methionine, homocysteine, cystathionine, or cysteine, whereas the modified strain has lost that ability.

a1) Introduction of the gene metY, a heterologous gene from *C. glutamicum*. This gene is to evolve from an acetylhomoserine sulfhydrylase activity into a cysteine-synthase activity.

b) Culture of the modified strain *E. coli* [metY Δ(cysK, cysM)] on the same minimal medium (MM) with no co-substrate, to cause the evolution of MetY into a cysteine-synthase activity to compensate for the initially deleted enzyme activities (CysK, CysM).

c) Selection of an evolved strain with a new cysteine-synthase activity in the presence of endogenous $H_2S$; verification of the new synthesis pathway.

Example F.II.1

Evolution of an Acetylhomoserine Sulfhydrylase Activity into a Cysteine Synthase Activity a) Construction of the Strain *E. coli* Δ(cysK, cysM)

The inactivation of the genes cysK and cysM is carried out by inserting an antibiotic resistance cassette (chloramphenicol and kanamycin respectively) while at the same time deleting most of the genes concerned. The method used is described by Datsenko, K. A.; Wanner, B. L. (2000), One-step inactivation of chromosomal genes in *Escherichia coli* K-12 using PCR products. *Proc. Natl. Acad. Sci. USA* 97: 6640-6645. For each construction a pair of oligonucleotides is synthesized:

For cysK:
DcysKR with 100 bases (SEQ ID NO 15):

```
Tgttgcaattctttctcagtgaagagatcggcaaacaatgcggtgcttaaataacgctcacccgatgatggtagaa
taacCATATGAATATCCTCCTTAG
``` with a region (lower case) homologous to the sequence (2531396 to 2531317) of the gene cysK, a region (upper case) for the amplification of the chloramphenicol resistance cassette (reference sequence in Datsenko, K. A. & Wanner, B. L., 2000, PNAS, 97: 6640-6645).

DcysKF de 100 bases (SEQ ID NO 16):

```
agtaagattttttgaagataactcgctgactatcggtcacacgccgctggttcgcctgaatcgcatcggtaacggac
gcatTGTAGGCTGGAGCTGCTTCG
``` with:
- a region (lower case) homologous to the sequence (2530432 a 2530511) of the gene cysK,
- a region (upper case) for the amplification of the chloramphenicol resistance cassette.

Pour cysM:
DcysMiR with 100 bases (SEQ ID NO 17):

```
cccgcccctggctaaaatgctcttccccaaacacccggtagaaaggtagcgatcgccacgatcgcagatgatcg
ccacCATATGAATATCCTCCTTAG
``` with:
- a region (lower case) homologous to the sequence (2536699 to 2536778) of the gene cysM,
- a region (upper case) for the amplification of the kanamycin resistance cassette.

DcysMF with 100 bases (SEQ ID NO 18):

```
Agtacattagaacaaacaataggcaatacgcctctggtgaagttgcagcgaatggggccggataacggcagtgaag
tgtgTGTAGGCTGGAGCTGCTTCG
``` with:
- a region (lower case) homologous to the sequence (2537600 to 2537521) of the gene cysM,
- a region (upper case) for the amplification of the kanamycin resistance cassette.

The oligonucleotides DcysKR and DcysKF, and DcysMR and DcysMF are used respectively to amplify the chloramphenicol and kanamycin resistance cassettes from plasmids pKD3 and pKD4. The PCR product obtained is then introduced by electroporation in the strain MG1655 (pKD46) in which the enzyme Red recombinase expressed permits the homologous recombination. The transformants resistant to each of the antibiotics are then selected and the insertion of the resistance cassette is verified by a PCR analysis with the oligonucleotides cysKR and cysKF, and cysMR and cysMF.

cyKR (SEQ ID NO 19): tttttaacagacgcgacgcacgaagagcgc (homologous to the sequence from 2531698 to 2531669)
cysKF (SEQ ID NO 20): ggcgcgacggcgatgtgggtcgattgctat (homologous to the sequence from 2530188 to 2530217)
cysMR (SEQ ID NO 21): ggggtgacggtcaggactcaccaatacttc (homologous to the sequence from 2536430 to 2536459)
cysMF (SEQ ID NO 22): gcgcgcatcgctggccgctgggctacacac (homologous to the sequence from 2538071 to 2538042).

The chloramphenicol and kanamycin resistance cassettes can then be eliminated. For this purpose the plasmid pCP20, carrying FLP recombinase acting at the FRT sites of the chloramphenicol or kanamycin resistance cassettes, is introduced into the recombinant strains by electroporation. After a series of cultures at 42° C., the loss of the antibiotic resistance cassette is verified by a PCR analysis with the same oligonucleotides as used previously.

a1) Introduction of the Gene metY in the Preceding Strain

The plasmid pTopometY is constructed by insertion of the gene metY in the vector Zero Blunt TOPO PCR cloning kit (PCR4 TOPO vector, Invitrogen). For this purpose the gene metY is amplified by PCR with the polymerase Pwo from the chromosomal DNA of the strain *Corynebacterium glutamicum* ATCC13032 using the following oligonucleotides:

MetYR (SEQ ID NO 23):

```
ttagagctgttgacaattaatcatccggctcgtataatgtgtggaataaaaactcttaaggacctccaaatgcc
```

Promoter of type TRC (pTRC-O) in bold roman, RBS of the gene metY in bold roman underlined, initiation codon of the gene metY in bold italics.

MetYF (SEQ ID NO 24):

```
gctctgtctagtctagtttgcattctcacg
```

Sequence chosen downstream of the transcription terminator metY.

The PCR product obtained is then directly cloned in the vector Topo to give the plasmid pTopometY. The vector Topo carries a replication origin for *E. coli*, an ampicillin resistance gene and a kanamycin resistance gene.

The plasmid pTopometY is then introduced into the strain *E. coli* DH5α for verification of the construction. The sequencing of the gene metY of the plasmid pTopometY with the universal oligonucleotides M13 reverse and M13 forward is then carried out to confirm the construction.

The plasmid is introduced into the strain *E. coli* Δ(cysK, cysM) by electroporation.

c) Culture of the Modified Strain to Cause the Gene metY Coding for Acetyl-Homoserine Sulfhydrylase Activity to Evolve Toward a Cysteine Synthase Activity The controlled selection of the preceding strain containing the gene metY can be carried out in bottles or conical flasks.

The implementation of this method permits the selection of a strain of *Escherichia coli* in which the enzyme acetyl-homoserine sulfhydrolase has evolved into a 'cysteine synthase' activity. The controlled selection is performed in conical flasks containing 50 ml of inorganic medium (Schaefer et al., 1999, *Anal. Biochem.* 270: 88-96) in the presence of 33 mM glucose, chloramphenicol at a final concentration of 25 mg/l and kanamycin at a concentration of 25 mg/l.

The culture media are seeded with the strain *E. coli* K12 [Δ(cysK, cysM) pTopometY] at a defined $OD_{600\ nm}$ value. Seeding is carried out with a population of bacteria sufficiently large for some bacteria potentially to possess relevant mutations in the gene metY enabling them to assimilate O-acetyl serine. This population is obtained by growing the strain auxotrophic for cysteine on a cysteine-supplemented minimal medium. A control culture is seeded with the strain *E. coli* K12 (ΔcysK, cysM).

The cultures are carried out with shaking at 37° C., for 6 days, after which time the $OD_{600\ nm}$ is measured. The control culture displays practically no change in OD, while some other cultures exhibit significant evolution of their OD. It is therefore probable that the 'evolved cysteine synthase activity' has appeared in the populations contained in those conical flasks. The mutation or mutations probably occurr in the gene metY because this gene was the only difference between these strains and the control strain.

The bacterial population of these positive cultures can then be used to further improve the cysteine synthase activity by repeating the flask culture procedure as described.

c) Selection of Clones

The evolved population is then spread on a gelosed minimal medium containing glucose as sole carbon source. The inoculated dishes are placed in aerobic conditions in an incubator at 37° C. After 36 hours, the clones appear on the dishes; they correspond to bacteria able to produce cysteine from glucose as sole carbon source. Three clones are isolated Control of the Synthesis Pathway The population of evolved *E. coil* K12 [Δ(cysK, cysM) pTopometY] is cultured in a minimal medium (Schaefer et al., 1999, *Anal. Biochem.* 270: 88-96) containing 2,5 $g.l^{-1}$ of glucose uniformly labeled with carbon 13. After culture, the cells were recovered, washed and hydrolysed with 6N HCl for 24 hours at 107° C. A 2D NMR analysis was then performed (HSQC). This analysis allows the fate of the glucose carbon 13 to be determined, thereby confirming that the synthesis of cysteine takes place via serine and acetyl-serine, indicating that the enzyme coded for by the gene metY has evolved into a cysteine synthase.

F.III. Evolution of NADPH-Dependent Enzymes

One application (Example F.III.1.) of the invention to metabolic engineering of NADPH-dependent bioconversion pathways comprises the following steps:

a1) Inactivation of the genes udhA and pgi in the initial strain *E. coli;* a2) Inactivation of the genes pfkA, pfkB and udhA in the initial strain *E. coli;*

The resulting modified strains are thus optimized for their ability to reduce NADP.

The initial strain is able to grow on a minimal medium (MM), while the ability of the modified strains to grow on that medium is strongly impaired.

b) Introduction of a plasmid harboring the gene yueD coding for a benzyl reductase of *Bacillus cereus.* c) Culture of the preceding modified strain on the minimal medium (MM) to which is added p-nitrobenzaldehyde (co-substrate) to cause the evolution of the benzyl reductase activity for that poorly metabolized substrate.

d) Characterization of the evolved enzyme YueD

Example F.III.1

Construction of the Strains *E. coli* Δ(udhA, pgi) and *E. coli* Δ(pfkA, pfkB, udhA) and Modification of the Kinetic Characteristics of the Benzyl Reductase of *Bacillus cereus* a1) Construction of the Modified Strain *E. coli* Δ(udhA, pgi)

The inactivation of the gene udhA, is carried out by inserting an antibiotic resistance cassette conferring resistance to kanamycin while at the same time deleting most of the gene concerned. The method used is described by Datsenko, K. A.; Wanner, B. L. (2000), One-step inactivation of chromosomal genes in *Escherichia coli* K-12 using PCR products. *Proc. Natl. Acad. Sci. USA* 97: 6640-6645.

For this purpose two oligonucleotides are synthesized:
DudhAR with 100 bases (SEQ ID NO 25):

```
cccagaatctcttttgtttcccgatggaacaaaattttcagcgtgcccacgttcatgccgacgatttgtgcgcgtg ccagTGTAGGCTGGAGCTGCTTCG
``` with
a region (lower case) homologous to the sequence (4157144 to 4157223) of the gene udhA,
a region (upper case) for the amplification of the kanamycin resistance cassette (reference sequence in Datsenko, K. A. & Wanner, B. L., 2000, PNAS, 97: 6640-6645).

DudhAF with 100 bases (SEQ ID NO 26):

```
ggtgcgcgcgtcgcagttatcgagcgttatcaaaatgttggcggcggttgcacccactggggcaccatcccgtcga aagcCATATGAATATCCTCCTTAG
``` with:
a region (lower case) homologous to the sequence (4158285 to 4158206) of the gene udhA,
a region (upper case) for the amplification of the kanamycin resistance cassette.

The oligonucleotides DudhAR and DudhAF are used to amplify the kanamycin resistance cassette from the plasmid pKD4. The PCR product obtained is then introduced by electroporation into the strain MG1655 (pKD46) in which the Red recombinase enzyme expressed permits the homologous recombination. The kanamycin resistant transformants are then selected and the insertion of the resistance cassette is verified by a PCR analysis with the oligonucleotides UdhAR and UdhAF UdhAR (SEQ ID NO 27): gcgggatcacmactgccagcgctggctg
(homologous to the sequence 4156772 to 4156801)

UdhAF (SEQ ID NO 28): ggccgctcaggatatagccagataaatgac
(homologous to the sequence 4158475 to 4158446)

The inactivation of the gene pgi, is carried out by inserting an antibiotic resistance cassette conferring resistance to chloramphenicol while at the same time deleting most of the gene concerned. The method used is described by Datsenko, K. A.; Wanner, B. L. (2000), One-step inactivation of chromosomal genes in *Escherichia coli* K-12 using PCR products. *Proc. Natl. Acad. Sci. USA* 97: 6640-6645.

For this purpose two oligonucleotides are synthesized:
DpgiR with 100 bases (SEQ IID NO 29):

```
gcgccacgctttatagcggttaatcagaccattggtcgagctatcgtggctgctgatttctttatcatctttcagc tctgCATATGAATATCCTCCTTAG
``` with
- a region (lower case) homologous to the sequence (4232980 to 4232901) of the gene pgi,
- a region (upper case) for the amplification of the chloramphenicol resistance cassette (reference sequence in Datsenko, K. A. & Wanner, B. L., 2000, PNAS, 97: 6640-6645).

DpgiF with 100 bases (SEQ ID NO 30):

```
ccaacgcagaccgctgcctggcaggcactacagaaacacttcgatgaaatgaaagacgttacgatcgccgatcttt ttgcTGTAGGCTGGAGCTGCTTCG
``` with:
- a region (lower case) homologous to the sequence (4231352 to 4231432) of the gene pgi,
- a region (upper case) for the amplification of the chloramphenicol resistance cassette.

The oligonucleotides DpgiR and DpgiF are used to amplify the chloramphenicol resistance cassette from the plasmid pKD3. The PCR product obtained is then introduced by electroporation into the strain MG1655 ΔudhA (pKD46) in which the Red recombinase enzyme expressed permits the homologous recombination. The chloramphenicol resistant transformants are then selected and the insertion of the resistance cassette is verified by a PCR analysis with the oligonucleotides PgiR and PgiF PgiR (SEQ ID NO 31): cggtatgatttccgttaaattacagacaag
(homologous to the sequence 4233220 to 4233191)

PgiF (SEQ ID NO 32): gcggggcggttgtcaacgatggggtcatgc
(homologous to the sequence 4231138 to 4231167)

The two antibiotic resistance cassettes can then be eliminated. The plasmid pCP20 carrying recombinase FLP acting at the FRT sites of both the kanamycin and chloramphenicol resistance cassette is then introduced into the recombinant strains by electroporation. After a series of cultures at 42° C., the loss of the two resistance cassettes is verified by a PCR analysis with the same oligonucleotides as those used previously. The strain retained is designated MG1655 Δ(pgi, udhA).

a2) Construction of the Modified Strain *E. coli* Δ(pfkA, pfkB, udhA)

The inactivation of the gene pfkA, is carried out by inserting an antibiotic resistance cassette conferring resistance to chloramphenicol while at the same time deleting most of the gene concerned. The method used is described by Datsenko, K. A.; Wanner, B. L. (2000), One-step inactivation of chromosomal genes in *Escherichia coli* K-12 using PCR products. *Proc. Natl. Acad. Sci. USA* 97: 6640-6645.

For this purpose two oligonucleotides are synthesized:

DpfkAR with 100 bases (SEQ ID NO 33):

```
ttcgcgcagtccagccagtcacctttgaacggacgcttcatgttttcgatagcgtcgatgatgtcgtggtgaacca gctgCATATGAATATCCTCCTTAG
``` with
- a region (lower case) homologous to the sequence (4106081 to 4106002) of the gene pikA,
- a region (upper case) for the amplification of the chloramphenicol resistance cassette (reference sequence in Datsenko, K. A. & Wanner, B. L., 2000, PNAS, 97: 6640-6645).

DpfkAF de 100 bases (SEQ ID NO 34):

```
ggtgtgttgacaagcggcggtgatgcgccaggcatgaacgccgcaattcgcggggttgttcgttctgcgctgacag aaggTGTAGGCTGGAGCTGCTTCG
``` with:
a region (lower case) homologous to the sequence (4105147 to 4105227) of the gene pfkA,
a region (upper case) for the amplification of the chloramphenicol resistance cassette.

The oligonucleotides DpfkAR and DpfkAF are used to amplify the chloramphenicol resistance cassette from the plasmid pKD3. The PCR product obtained is then introduced by electroporation into the strain MG1655 (pKD46) in which the Red recombinase enzyme expressed permits the homologous recombination. The chloramphenicol resistant transformants are then selected and the insertion of the resistance cassette is verified by a PCR analysis with the oligonucleotides PfkAR and PfkAF PfkAR (SEQ ID NO 35): ccctacgccccacttgttcatcgcccg (homologous to the sequence 4106434 to 4106408)

PfkAF (SEQ ID NO 36): cgcacgcggcagtcagggccgacccgc (homologous to the sequence 4104751 to 4104777)

The inactivation of the udhA gene was described in example F.III.1 a1) and can be carried out in the same way.

The two antibiotic resistance cassette can then be eliminated. The plasmid pCP20 carrying recombinase FLP acting at the FRT sites of both the kanamycin and chloramphenicol resistance cassette is then introduced into the recombinant strains by electroporation. After a series of cultures at 42° C., the loss of the two resistance cassettes is verified by a PCR analysis with the same oligonucleotides as those used previously. The strain retained is designated MG1655 Δ(pfkA, udhA).

The inactivation of the gene pfkB, is carried out by inserting an antibiotic resistance cassette conferring resistance to chloramphenicol while at the same time deleting most of the gene concerned. The method used is described by Datsenko, K. A.; Wanner, B. L. (2000), One-step inactivation of chromosomal genes in *Escherichia coli* K-12 using PCR products. *Proc. Natl. Acad. Sci. USA* 97: 6640-6645.

For this purpose two oligonucleotides are synthesized:
DpfkBR with 100 bases (SEQ IID NO 37):

plasmid pKD3. The PCR product obtained is then introduced by electroporation into the strain MG1655 Δ(pfkA, udhA) (pKD46) in which the Red recombinase enzyme expressed permits the homologous recombination. The chloramphenicol resistant transformants are then selected and the insertion of the resistance cassette is verified by a PCR analysis with the oligonucleotides PfkBR and PfkBF PfkBR (SEQ ID NO 39): gccggttgcactttgggtaagccccg (homologous to the sequence 1805657 to 1805632)

PfkBF (SEQ ID NO 40): tggcaggatcatccatgacagtaaaaacgg (homologous to the sequence 1803996 to 1804025)

The chloramphenicol resistance cassette can then be eliminated. The plasmid pCP20 carrying recombinase FLP acting at the FRT sites of the chloramphenicol resistance cassette is then introduced into the recombinant strains by electroporation. After a series of cultures at 42° C., the loss of the chloramphenicol resistance cassette is verified by a PCR analysis with the same oligonucleotides as those used previously. The strain retained is designated MG1655 Δ(pfkA, pfkB, udhA).

a1) Introduction of the Gene yueD Coding for Benzil Reductase of *Bacillus cereus* into the Strain Δ(pgi, udhA) or Similarly Δ(pfkA, pfkB, udhA)

The gene yueD is cloned into the vector pTrc99A (Amersham-Pharmacia). The oligos YueDR and YueDF are used for the amplification of the gene from chromosomal DNA of *Bacillus cereus*.

YueDR (SEQ ID NO 41): CGTGAATTCttattcatcaat-tctaataa with:
a region (lower case) homologous to the sequence (731 to 750) of the gene yueD,
a region (upper case) allowing the cleavage by the enzyme EcoRI.

YueDF (SEQ ID NO 42): ACGTTCatgAgAtacgttatcataa-caggaac with:
a region (lower case) homologous to the sequence (1 to 26) of the gene yueD,

```
gcgggaaaggtaagcgtaaattttttgcgtatcgtcatgggagcacagacgtgttccctgattgagtgtggctgca ctccCATATGAATATCCTCCTTAG
``` with
a region (lower case) homologous to the sequence (1805320 to 1805241) of the gene pfkB,
a region (upper case) for the amplification of the chioramphenicol resistance cassette (reference sequence in Datsenko, K. A. & Wanner, B. L., 2000, PNAS, 97: 6640-6645).
DpfkBF with 100 bases (SEQ ID NO 38):

a region (changed and added bases, upper case) allowing the cleavage by the enzyme BspHI.

The PCR product obtained is digested with the restriction enzymes BspHI and EcoRI and cloned into the vector pTrc99A that has been digested with NcoI and EcoRI. The resulting plasmid pYU1 is then introduced into the strain MG1655 Δ(pgi, udhA). The gene yueD codes for a NADPH-

```
gcgccctctctcgatagcgcaacaattacccgcaaatttatcccgaaggaaaactgcgctgtaccgcaccggtgt tcgTGTAGGCTGGAGCTGCTTCG
``` with:
a region (lower case) homologous to the sequence (1804421 to 1804499) of the gene pfkB,
a region (upper case) for the amplification of the chloramphenicol resistance cassette.

The oligonucleotides DpfkBR and DpfkBF are used to amplify the chloramphenicol resistance cassette from the dependent benzil reductase that efficiently reduces 1-phenyl-1,2-propanedione ($k_{cat}$=165 min$^{-1}$; $K_m$=42 µM) but possesses a lower activity toward p-nitrobenzaldehyde ($k_{cat}$=1.2 min$^{-1}$; $K_m$=261 µM) (Maruyama, R. Nishizawa, M.; Itoi, Y.; Ito, S.; Inoue, M. (2002) The enzyme with benzil reductase activity is conserved from bacteria to mammals. *J. Biotechnology* 94: 157-169).

b) Culture and Evolution of the Modified Strain on a Minimal Medium

The maximal growth rate of the strain of *E. coli* [Δ(udhA, pgi) yueD] obtained is evaluated on minimal medium ($\mu_{max}$=0.04). In these conditions it is much lower than that of the unmodified strain ($\mu_{max}$=0.61). It is then decided to add 1-phenyl-1,2-propanedione (co-substrate) to the minimal medium, and it is found that the modified strain is able to grow at a rate slightly inferior to that of the initial (i.e., unmodified) strain on the same medium. It is then decided to seed (OD 5) a chemostat in a minimal medium containing p-nitrobenzaldehyde (co-substrate) with the modified strain; in these conditions the strain exhibits a growth rate similar to that of the modified strain grown on a minimal medium with no co-substrate. The chemostat is maintained for 1 to 5 weeks, while gradually increasing the dilution rate. The increase in the dilution rate can be performed stepwise or continuously. Glycerol stocks of the population contained in the chemostat are made up regularly.

d) Characterization of the Evolved Enzyme YueD

When the population can no longer adapt to the dilution rates imposed, it is considered that the selection is completed. Single colonies are isolated from the final evolved population (if necessary using one of the last glycerol stocks made up) and the kinetic characteristics of the evolved benzil reductase are evaluated, by comparison with the initial benzil reductase, using substrates 1-phenyl-1,2-propanedione and p-nitrobenzaldehyde. The $k_{cat}$ value for the evolved benzil reductase is markedly improved for p-nitrobenzaldehyde, while its $k_{cat}$ for 1-phenyl-1,2-propanedione is strongly depressed. Sequencing of the evolved clones demonstrates an accumulation of point mutations, which explains the altered substrate specificity of these enzymes.

REFERENCES

Anderson, E. H. (1946), Growth requirements of virus-resistant mutants of *Escherichia coli* strain "B" *Proc. Natl. Acad. Sci. USA* 32:120-128.

A Baudin, O Ozier-Kalogeropoulos, A Denouel, F Lacroute, and C Cullin (1993), A simple and efficient method for direct gene deletion in *Saccharomyces cerevisiae*, *Nucl. Acids Res.,* 21: 3329-3330, 1993.

Brachmann C B, Davies A, Cost G J, Caputo E, Li J, Hieter P, Boeke J D. (1998), Designer deletion strains derived from *Saccharomyces cerevisiae* S288C: a useful set of strains and plasmids for PCR-mediated gene disruption and other applications. *Yeast.* 14:115-32.

Datsenko, K. A.; Wanner, B. L. (2000), One-step inactivation of chromosomal genes in *Escherichia coli* K-12 using PCR products. *Proc. Natl. Acad. Sci. USA* 97: 6640-6645.

Miller, 1992. A Short Course in Bacterial Genetics: A Laboratory Manual and Handbook for *Escherichia coli* and Related Bacteria, Cold Spring Harbor Laboratory Press, Cold Spring Harbor, N.Y.

Sambrook et al. (1989), Molecular cloning: a laboratory manual. $2^{nd}$ Ed. Cold Spring Harbor Lab., Cold Spring Harbor, N.Y.

Schaefer, U., Boos, W., Takors, R., Weuster-Botz, D. (1999), Automated sampling device for monitoring intracellular metabolite dynamics, *Anal. Biochem.* 270: 88-96.

Wach, A., Brachat, A., Pohlmann, R., and Philippsen, P. (1994) New heterologous modules for classical or PCR-based gene disruptions in *Saccharomyces cerevisiae. Yeast,* 10, 1793-1808.

---

What is claimed is:

1. A method for producing a microorganism wherein said microorganism is obtained by selection of a modified microorganism, having a modified methionine biosynthesis pathway for the biosynthesis of methionine by metabolism of a simple carbon source and methylmercaptan as a source of sulfur, comprising:
   a) generating a modified microorganism by inactivating, deleting, or inhibiting expression of metE gene in an initial microorganism, wherein ability of said modified microorganism to grow is impaired when grown on a minimal medium containing no methionine, S-adenosylmethionine, homocysteine or cystathionine;
   b) culturing said modified microorganism obtained in step (a) on said minimal medium, in the presence of methylmercaptan under selection pressure thereby allowing said modified microorganism to proliferate through a methionine biosynthesis pathway to compensate for impaired growth; and
   c) selecting said microorganism from step (b) able to grow on said minimal medium in presence of methylmercptan,
   wherein the methionine biosynthesis pathway modifies such that methionine is produced by the metabolism of a simple carbon source and methylmercaptan as a source of sulfur thereby allowing said microorganism to proliferate on said minimal medium containing no methionine, S-adenosylmethionine, homocysteine or cystathionine.

2. The method as claimed in claim 1, wherein said microorganism possesses at least one modified gene coding for a modified protein-involved in the methionine biosynthesis pathway.

3. The method as claimed in claim 2, comprising a step d) comprising the isolation of said gene coding for a modified protein involved in the methionine biosynthesis pathway.

4. The method as claimed in claim 3, wherein said gene is introduced, into a production microorganism intended for the production of said protein.

5. The method of claim 1, wherein said inactivating, deleting, or inhibiting expression of the metE gene is performed by directed mutation of said metE gene or directed modification of a promoter of said metE gene.

6. The method of claim 1, wherein the deletion of the metE gene includes removal of most of said metE gene.

7. The method of claim 1, wherein said metE gene is replaced with a selection marker gene.

8. The method of claim 1, wherein said microorganism is a bacteria.

9. The method of claim 1, wherein said microorganism is an *Escherichia* sp.

10. The method of claim 1, wherein the microorganism is *E. coli*.

11. An evolved microorganism having a modified methionine biosynthesis pathway produced by the method of claim 1.

12. The method of claim 2, wherein said gene coding for said protein involved in the methionine biosynthesis pathway is a mutated metB gene with methionine synthase activity which allows for the direct conversion of O-succinyl-L-homoserine into L-methionine with methylmercaptan as a sulfur source.

13. The method of claim 3, wherein said gene coding for said protein involved in the methionine biosynthesis pathway is a mutated metB gene with methionine synthase activity which allows for the direct conversion of O-succinyl-L-homoserine into L-methionine with methylmercaptan as a sulfur source.

14. A method for preparation of modified strains of *E. coil* having a modified methionine biosynthesis pathway for the biosynthesis of methionine by metabolism of a simple carbon source and methylmercaptan as a source of sulfur, comprising:
   (a) generating a modified microorganism by inactivating, deleting, or inhibiting expression of metE gene in an initial *E. coil* strain, wherein ability of said modified microorganism to grow is impaired when grown on a minimal medium containing no methionine, S-adenosylmethionine, homocysteine or cystathionine,
   b) culturing said modified microorganism obtained in step (a) on said minimal medium in presence of methylmercaptan under selection pressure thereby allowing said modified microorganism to proliferate through the methionine biosynthesis pathway to compensate for the impaired growth; and
   c) selecting an-evolved said *E. coil* strain from step (b) able to grow on said minimal medium in the presence of methylmercptan, said microorganism comprising a mutated metB gene with methionine synthase activity and allowing the direct conversion of O-succinyl-L-homoserine into L-methionine with methylmercaptan as a sulfur source.

15. The method of claim 14, wherein said deletion includes the removal of most of said metE gene.

16. The method of claim 14, wherein said metE gene is replaced with a selection marker gene.

17. The method of claim 14, wherein said initial *E. coli* strain is strain *E. coli* K12.

18. The method of claim 14, wherein said *E. coil* strain is strain *E. coil* 183 deposited at the Collection Nationale de Cultures de Microorganisms (CNCM) and registered under the number I-3005.

19. The method of claim 1, wherein said simple carbon source is selected from the group consisting of glucose, galactose, sucrose, lactose and molasses.

* * * * *